(12) United States Patent
Sun

(10) Patent No.: US 9,427,441 B2
(45) Date of Patent: Aug. 30, 2016

(54) TARGETING PRIMARY CILIA TO TREAT GLAUCOMA

(71) Applicant: Indiana University Research and Technology Corporation, Indianapolis, IN (US)

(72) Inventor: Yang Sun, Indianapolis, IN (US)

(73) Assignee: Indiana University Research and Technology Corporation, Indianapolis, IN (US)

(*) Notice: Subject to any disclaimer, the term of this patent is extended or adjusted under 35 U.S.C. 154(b) by 17 days.

(21) Appl. No.: 14/626,101

(22) Filed: Feb. 19, 2015

(65) Prior Publication Data

US 2015/0231148 A1    Aug. 20, 2015

Related U.S. Application Data

(60) Provisional application No. 61/941,601, filed on Feb. 19, 2014.

(51) Int. Cl.
| | | |
|---|---|---|
| *A61K 31/496* | (2006.01) | |
| *A61K 31/55* | (2006.01) | |
| *A61K 31/381* | (2006.01) | |
| *A61K 9/00* | (2006.01) | |

(52) U.S. Cl.
CPC ............ *A61K 31/55* (2013.01); *A61K 9/0048* (2013.01); *A61K 31/381* (2013.01); *A61K 31/496* (2013.01)

(58) Field of Classification Search
CPC ................................................. A61K 31/496
See application file for complete search history.

(56) References Cited

U.S. PATENT DOCUMENTS

2007/0259856 A1   11/2007   Kumar et al.

FOREIGN PATENT DOCUMENTS

| WO | 0003687 A2 | 1/2000 | |
|---|---|---|---|
| WO | 0195911 A1 | 12/2001 | |
| WO | 0217924 A1 | 3/2002 | |
| WO | 2006029209 A2 | 3/2006 | |
| WO | WO 2013169396 | * 11/2013 | ........... C07D 207/30 |

OTHER PUBLICATIONS

Wei et al. (Bioorganic & Medicinal Chemistry Letters, Available online Jul. 6, 2015, doi:10.1016/j.bmcl.2015.06.098).*
Kubinyi (3D QSAR in Drug Design: Ligand-Protein Interactions and Molecular Similarity, vol. 2-3, Springer, 1998, 800 pages). p. 243-44 provided.*
Wermuth, The Practice of Medicinal Chemsitry, 2d ed. (2003), 768 pages. Chs. 9-10 provided.*
Park et al. (Toxicology Lett., 120 (2001), 281-91).*
Ryskamp et al. (J Neurosci., May 11, 2011; 31(19): 7089-7101).*
Smith, et al., The transmembrane protein meckelin (MKS3) is mutated in Meckel-Gruber syndrome and the wpk rat, Nat. Genet., 2006, 38(2): pp. 191-196.
Tripathi, R.C., and Tripathi, B.J., Human trabecular endothelium, corneal endothelium, keratocytes, and scleral fibroblasts in primary cell culture. A comparative study of growth characteristics, morphology, and phagocytic activity by light and scanning electron microscopy, (Exp. Eye Res.), 1982, 35(6), pp. 611-624.
Luo, et al., OCRL localizes to the primary cilium: a new role for cilia in Lowe syndrome, (Hum. Mol. Genet. 2012, 21 (15), pp. 3333-3344 (Journal)).
Kang, et al., Regulation of SPARC by Transforming Growth Factor β2 in Human Trabecular Meshwork, Invest. Ophthalmol. Vis. Sci. 2013, 54(4), pp. 2523-2532).
Mandel, et al., Hydrostatic Pressure—Induced Release of Stored Calcium in Cultured Rat Optic Nerve Head Astrocytes, (Invest. Ophthalmol. Vis. Sci. 2010, 51(6), pp. 3129-3138).
Touw, et al., Altered calcium signaling in colonic smooth muscle of type 1 diabetic mice., Am. J. Physiol. Gastro. Liver Physiology 2012, 302(1):G66-76.
Blitzer, et al. Primary cilia dynamics instruct tissue patterning and repair of corneal endothelium, (Proc. Natl. Acad. Sci. USA 2011, 108(7), pp. 2819-2824.
Coon, et al. The Lowe syndrome protein OCRL1 is involved in primary cilia assembly, (Hum. Mol. Genet. 2012, 21(8), pp. 1835-1847.
Alward, et al., Clinical Features Associated with Mutations in the Chromosome 1 Open-Angle Glaucoma Gene (GLC1A), N. Engl. J. Med. 1998, 338(15), pp. 1022-1027).
Attree, et al., Comprehensive Pediatric Nephrology: Text with CD-ROM, Nature 1992, 358(6383), pp. 239-242.

* cited by examiner

*Primary Examiner* — Robert Havlin

(74) *Attorney, Agent, or Firm* — Stinson Leonard Street LLP

(57) ABSTRACT

Methods for reducing intraocular pressure and treating glaucoma are disclosed. The methods include administering to an individual a composition comprising a TRPV4 agonist.

13 Claims, 40 Drawing Sheets
(16 of 40 Drawing Sheet(s) Filed in Color)

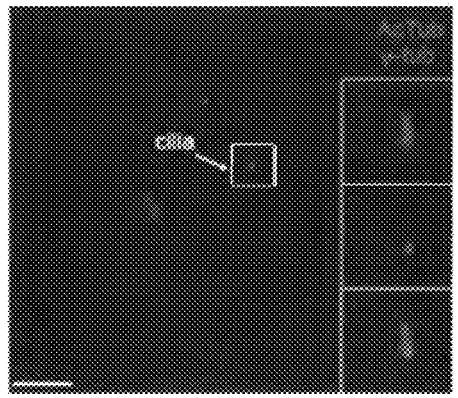 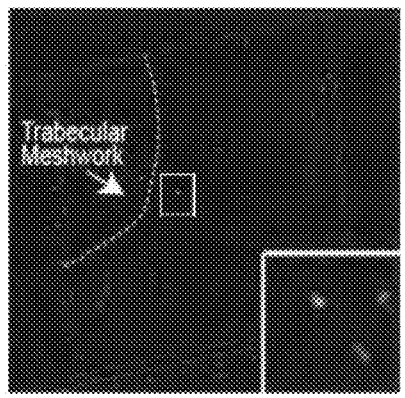
FIG. 2I  FIG. 2J
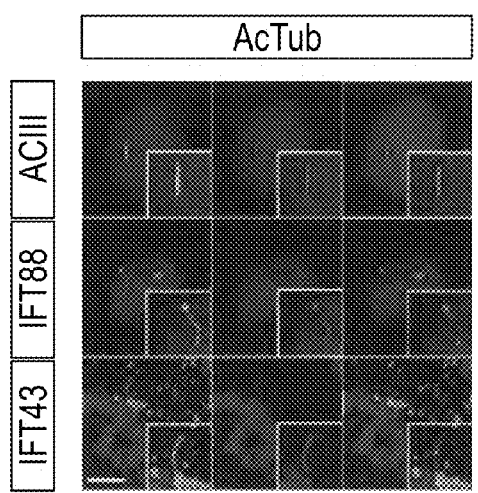 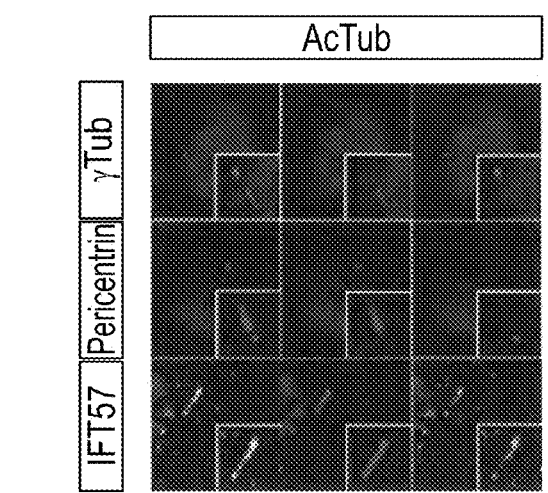
FIG. 2K

TARGETING PRIMARY CILIA TO TREAT GLAUCOMA

CROSS REFERENCE TO RELATED APPLICATION

This application claims priority to U.S. Provisional Patent Application No. 61/941,601 filed on Feb. 19, 2014, which is hereby incorporated by reference in its entirety.

STATEMENT REGARDING FEDERALLY SPONSORED RESEARCH OR DEVELOPMENT

This invention was made with government support under EY022058 awarded by National Institutes of Health. The Government has certain rights in the invention.

STATEMENT IN SUPPORT FOR FILING A SEQUENCE LISTING

A paper copy of the Sequence Listing and a computer readable form of the Sequence Listing containing the file named "IURTC 2014-099-02_ST25.txt", which is 730 bytes in size (as measured in MICROSOFT WINDOWS® EXPLORER), are provided herein and are herein incorporated by reference. This Sequence Listing consists of SEQ ID NOs:1-3.

BACKGROUND OF THE DISCLOSURE

The present disclosure relates generally to treating diseases and disorders resulting from defects in cilia formation, cilia maintenance and cilia function. More particularly, the present disclosure relates to methods for reducing eye pressure, methods for treating ciliopathies and methods for treating glaucoma by administering transient receptor potential cation channel subfamily V member 4 (TRVP4) agonists.

The primary cilium is an evolutionarily conserved subcellular structure that protrudes from many post-mitotic eukaryotic cells. In response to changes in the extracellular environment, primary cilia coordinate signaling cascades that control cell differentiation, growth and function. A highly specialized extension of the plasma membrane, the ciliary membrane is enriched with many signaling proteins, including Transient Receptor Potential (TRP) channels. Upon extracellular stimulation, TRP channels initiate signal transduction cascades by inducing $Ca^{2+}$ flow. Phosphoinositides within the ciliary membrane are essential secondary messengers for ciliary function, potentially through modulation of the activities of TRP channels.

Transient receptor potential cation channel subfamily V member 4 (TRPV4) is a member of the OSM9-like transient receptor potential channel (OTRPC) subfamily that in humans is encoded by the TRPV4 gene. TRPV4 protein is a $Ca^{2+}$-permeable, nonselective cation channel that is thought to be involved in the regulation of systemic osmotic pressure. TRPV4 also functions as a ciliary mechanosensory channel. Mutations in the TRPV4 gene have been associated with disorders including brachyolmia type 3, congenital distal spinal muscular atrophy, scapuloperoneal spinal muscular atrophy and subtype 2C of Charcot-Marie-Tooth disease. A number of TRPV4 agonists and antagonists have been identified including, for example, the antagonist Ruthenium Red, the agonist 4aPDD, the selective antagonist RN-1734, the agonist GSK1016790A and the antagonist HC-067047.

Defects in cilia formation or maintenance underlie a wide range of human diseases, including retinitis pigmentosa, renal cysts, polydactyly, and developmental delays, which are collectively called ciliopathies. It has been discovered that OCRL, an inositol polyphosphate 5-phosphatase implicated in Oculocerebrorenal syndrome of Lowe (Lowe syndrome), a rare X-linked recessive disorder that presents in males with bilateral cataracts and glaucoma, as well as renal failure, muscular hypotonia, and mental retardation, regulates cilia biogenesis. OCRL substrates include phosphatidylinositol-4,5-bisphophatase [$PI(4,5)P_2$] and phosphatidylinositol-3,4,5-triphosphate [$PI(3,4,5)P_3$]. Decreased 5-phosphatase activity is demonstrated in fibroblasts from Lowe patients, as well as a two- to threefold elevated ratio of $PI(4,5)P_2:PI(4)P$.

Mechanosensation of pressure underlies a number of important human diseases including the development of hypertension and glaucoma. In the kidney epithelium, ciliary proteins polycystins (PC1/2) have been shown to be important for flow-dependent calcium flux. In the lining of the ventricles of the brain, cerebrospinal fluid is regulated by cilia. Similar to the kidney, the eye is an enclosed organ with sensitive homeostatic regulation of fluid production and egress. Defective sensation of pressure may result in imbalance of aqueous humor, resulting in elevated intraocular pressure. Low levels of eye pressure result in structural changes of the retina and poor vision, while elevated eye pressure may damage the optical nerve. Glaucoma is an optic neuropathy associated with elevated intraocular pressure and is a leading cause of irreversible blindness in the world.

Trabecular meshwork cells are responsible for the drainage of the majority of aqueous fluid. Dysfunction of the trabecular outflow leads to elevated intraocular pressure, which in susceptible individuals, results in the death of retinal ganglion cells that leads to irreversible vision loss. However, the molecular events whereby elevated pressure results in aberrant mechanosensory signaling that lead to visual loss are poorly understood. As disclosed herein, trabecular meshwork cells of the eye have primary cilia that are responsive to pressure changes.

Consistent with the central role of increased pressure in the pathology of glaucoma, the only proven treatment is lowering of pressure. Five classes of medications are available for treating glaucoma, which include beta blockers, alpha adrenergic agonists, carbonic anhydrase inhibitors, cholinergic agonists and prostaglandin analogs. Many patients become intolerant of the side effects of these medications. It is also recognized that these medications cease to lower pressure after a number of years. As patients become intolerant of medications and as the medications lose their effectiveness, surgical intervention is required to lower pressure.

Accordingly, there exists a need to develop alternative treatments for lowering eye pressure.

BRIEF DESCRIPTION OF THE DISCLOSURE

The present disclosure relates generally to treating diseases and disorders resulting from defects in cilia formation, cilia maintenance and cilia function. More particularly, the present disclosure relates to methods for reducing eye pressure, methods for treating ciliopathies and methods for treating glaucoma by administering transient receptor potential cation channel subfamily V member 4 (TRVP4) agonists.

In one aspect, the present disclosure is directed to a method for reducing intraocular pressure in an individual in need thereof. The method includes administering a TRPV4 agonist to the individual.

In another aspect, the present disclosure is directed to a method for treating glaucoma in an individual in need thereof. The method includes administering a TRPV4 agonist to the individual.

In another aspect, the present disclosure is directed to treating a ciliopathy in an individual in need thereof. The method includes administering a TRPV4 agonist to the individual.

In another aspect, the present disclosure is directed to a pharmaceutical formulation for reducing intraocular pressure including: from about 50 ng/g body weight to about 500 ng/g body weight a TRPV4 agonist.

In accordance with the present disclosure, methods have been discovered that surprisingly allow for the treatment for intraocular pressure and, in particular, glaucoma. The present disclosure has a broad and significant impact, as it allows for treating glaucoma and dysregulation of eye pressure that can lead to vision loss and blindness.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The disclosure will be better understood, and features, aspects and advantages other than those set forth above will become apparent when consideration is given to the following detailed description thereof. Such detailed description makes reference to the following drawings, wherein:

FIGS. 2I and 2J are fluorescence micrographs of trabecular meshwork cilia from bovine eyes stained with anti-Arl13b (AcTub, red) anti-α-tubulin (red), anti-γ-tubulin and (γ-Tub, green) and DAPI (blue), as discussed in Example 1. Scale bar=10 μm.

FIG. 2K are immunofluorescent micrographs of HTM cells serum-starved to induce ciliogenesis and immunostained with anti-Arl13b (red), anti-acetylated α-tubulin (AcTub, red), anti-IFT-88 (green), anti-IFT43 (green), anti-IFT57 (green), anti-adenylate cyclase III (AC III, green), anti-pericentrin (green), anti-γ-tubulin (γ-Tub, green) and DAPI (blue), as discussed in Example 1. Insets show higher magnification of cilia. Scale bar=5 μm.

Figure 1:
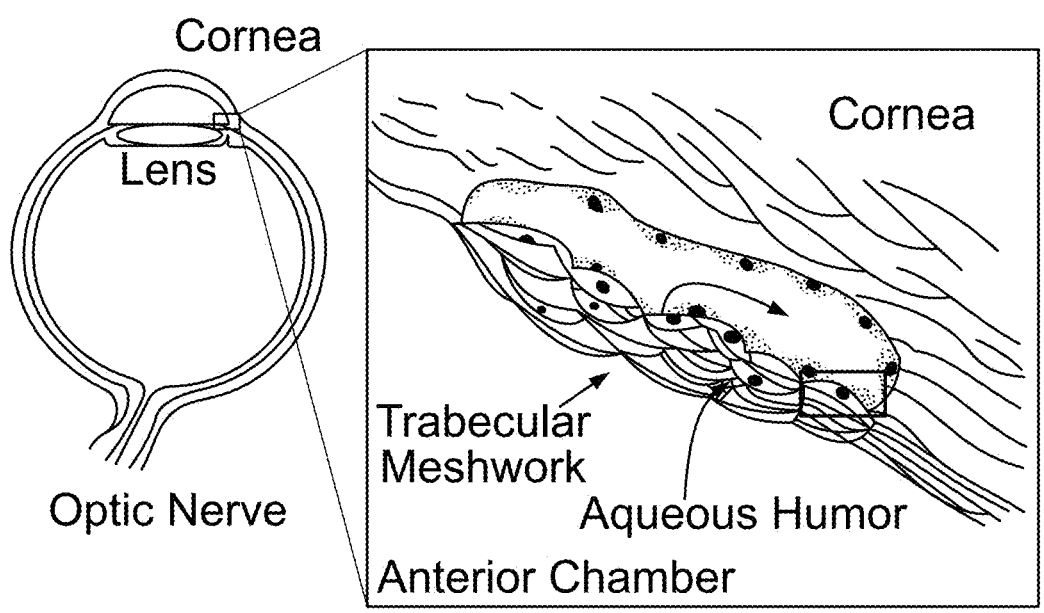
FIG. 1 is a schematic illustration of aqueous humor outflow in the eye, as discussed in Example 1.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DETAILED DESCRIPTION OF THE DISCLOSURE

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

Although some forms of ciliopathies present with disease states of fluid dysregulation, including hydrocephalus, it has been previously unknown if elevated eye pressure may be caused by ciliary disease. Glaucoma is an optic neuropathy associated with elevated intraocular pressure (IOP) and is a leading cause of irreversible blindness in the world. Consistent with the central role of increased pressure in the pathology of glaucoma, the only proven treatment for glaucoma is to lower eye pressure. Trabecular meshwork (TM) cells are responsible for the drainage of the majority of aqueous fluid, and dysfunction of the trabecular outflow leads to elevated IOP. In susceptible individuals (e.g., Lowe patients), this results in the death of retinal ganglion cells, causing irreversible vision loss. However, prior to the present disclosure, the molecular events whereby elevated pressure results in aberrant mechanosensory signaling that leads to vision loss are poorly understood.

In accordance with the present disclosure, treatments have been discovered that surprisingly allow for treating diseases and disorders resulting from defects in cilia formation, cilia maintenance and cilia function. Elevated eye pressure can lead to vision loss, blindness and glaucoma. Advantageously, the methods of the present disclosure allow for lowering intraocular pressure as treatments for elevated eye pressure associated with vision loss, blindness and glaucoma, as well as treatments for ciliopathies.

In one aspect, the present disclosure is directed to a method for reducing intraocular pressure in an individual in need thereof. The method includes administering a TRPV4 agonist to the individual.

In another aspect, the present disclosure is directed to a method for treating glaucoma in an individual in need thereof. The method includes administering a TRPV4 agonist to the individual.

In another aspect, the present disclosure is directed to treating a ciliopathy in an individual in need thereof. The method includes administering a TRPV4 agonist to the individual. The ciliopathy can be, for example, retinitis pigmentosa, renal cysts, polydactyly, and developmental delays.

As used herein "transient receptor potential vanilloid 4 agonist" or "TRPV4 agonist" refers to any compound capable of activating or enhancing the biological activities of a TRPV4 channel receptor. Suitable agonists to TRPV4 channel receptors can be, for example, compounds included in the class of 3-oxohexahydro-1H-azepin, azepine and acyclic 1,3-diamine and derivatives of these compounds. Suitable TRPV4 agonists can be, for example, GSK1016790A (N-((1S)-1-{[4-((2S)-2-{[(2,4-dichlorophenyl)sulfonyl]amino}-3-hydroxypropanoyl)-1-piperazinyl]carbonyl}-3-methylbutyl)-1-benzothiophene-2-carboxamide); N-{(1S)-1-[({(4R)-1-[(4-chlorophenyl)sulfonyl]-3-oxohexahydro-1H-azepin-4-yl}amino)carbonyl]-3-methylbutyl}-1-benzothiophene-2-carboxamide; N-{(1S)-1-[({(4R)-1-[(4-fluorophenyl)sulfonyl]-3-oxohexahydro-1H-azepin-4-yl}amino)carbonyl]-3-methylbutyl}-1-benzothiophene-2-carboxamide; N-{(1S)-1-[({(4R)-1-[(2-cyanophenyl)sulfonyl]-3-oxohexahydro-1H-azepin-4-yl}amino)carbonyl]-3-methylbutyl}-1-methyl-1H-indole-2-carboxamide; N-{(1S)-1-[({(4R)-1-[(2-cyanophenyl)sulfonyl]hexahydro-1H-azepin-4-yl}amino)carbonyl]-3-methylbutyl}-1-methyl-1H-indole-2-carboxamide; N-{(1S)-1-[({3-[[(cyanophenyl)sulfonyl](methyl)amino]propyl}amino)carbonyl]-3-methylbutyl}-1-benzothiophene-2-carboxamide; and N-{(1S)-1-[({3-[[(2,4-dichlorophenyl)sulfonyl](methyl)amino]propyl}amino)carbonyl]-3-methylbutyl}-1-benzothiophene-2-carboxamide. Other suitable TRVP4 agonists are disclosed in US 2007/0259856 and International Patent Applications WO 2000/03687, WO 2001/095911, WO 2002/017924, and WO 2006/029209, which are incorporated by reference herein to the extent they are consistent herewith.

Suitable amounts of the TRPV4 agonist can have, for example, an EC50 value for TRPV4 channel receptor of about 1.0 μM. Particularly suitable amounts of the TRPV4 agonist can have, for example, an EC50 value for TRPV4 channel receptor of less than 1.0 μM. In another aspect, the agonist can have, for example, an EC50 value for TRPV4 channel receptor of about 10 nM. Particularly suitable amounts of the TRPV4 agonist can have, for example, an EC50 value for TRPV4 channel receptor of less than 10 nM. In another aspect, the agonist has an EC50 value for TRPV4 channel receptor of about 1.0 μM as measured by calcium influx in isolated trabecular meshwork cells, human trabecular meshwork cells, normal human fibroblasts, Lowe syndrome patient keratinocytes, or Lowe syndrome patient fibroblasts. In particular, the agonist has an EC50 value for TRPV4 channel receptor of less than 1.0 μM as measured by calcium influx in isolated trabecular meshwork cells, human trabecular meshwork cells, normal human fibroblasts, Lowe syndrome patient keratinocytes, or Lowe syndrome patient fibroblasts.

A particularly suitable dosage can be from about 50 ng/g body weight to about 500 ng/g body weight, including from about 50 ng/g body weight to about 250 ng/g body weight, including from about 50 ng/g body weight to about 100 ng/g body weight, and including about 50 ng/g body weight. Suitable dosage of a TRPV4 channel receptor agonist of the present disclosure will depend upon a number of factors including, for example, age and weight of an individual, at least one precise condition requiring treatment, severity of a condition, nature of a formulation, route of administration and combinations thereof. Ultimately, a suitable dosage can be readily determined by one skilled in the art such as, for example, a physician, a veterinarian, a scientist, and other medical and research professionals. For example, one skilled in the art can begin with a low dosage that can be increased until reaching the desired treatment outcome or result. Alternatively, one skilled in the art can begin with a high dosage that can be decreased until reaching a minimum dosage needed to achieve the desired treatment outcome or result.

As used herein and as is understood in the art "EC50" or "effective concentration 50%" refers to the molar concentration of an agonist that produces 50% of the maximum possible stimulatory response for that agonist. The maximum stimulatory response for each agonist can be determined experimentally by measuring the magnitude of the desired biological response elicited by increasing concentrations of agonist until a plateau is achieved.

As used herein and as is understood in the art "IC50" or "inhibitory concentration 50%" refers to the molar concentration of a compound (agonist, antagonist, or inhibitor) that produces 50% of the maximum possible inhibitory response for that compound. The maximum inhibitory response for each compound can be determined experimentally by measuring the extent of inhibition of the desired biological response elicited by increasing concentrations of agonist until a plateau is achieved.

Any suitable method known to those skilled in the art can be used for administering the TRPV4 agonist. Suitable methods for administering the TRPV4 agonist can be, for example, topically, periocularly, intraocularly, by intraocular injection and other types of administration methods known to those skilled in the art.

The TRPV4 agonist of the disclosure can be administered as a pharmaceutical composition comprising the TRPV4 agonist of interest in combination with one or more pharmaceutically acceptable carriers. As used herein, the phrase "pharmaceutically acceptable" refers to those ligands, materials, formulations, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier", as used herein, refers to a pharmaceutically acceptable material, formulation or vehicle, such as a liquid or solid filler, diluent, excipient, solvent or encapsulating material, involved in carrying or transporting the active compound from one organ or portion of the body, to another organ or portion of the body. Each carrier must be "acceptable" in the sense of being compatible with the other components of the composition (e.g., TRPV4 agonist) and not injurious to the individual. Lyophilized compositions, which may be reconstituted and administered, are also within the scope of the present disclosure.

Pharmaceutically acceptable carriers may be, for example, excipients, vehicles, diluents, and combinations thereof. For example, where the compositions are to be administered by the ophthalmic mucous membrane route, they may be formulated as eye drops or eye ointments. These compositions can be prepared by conventional means, and, if desired, the active compound (i.e., TRPV4 agonist) may be mixed with any conventional additive, such as an excipient, a binder, a disintegrating agent, a lubricant, a corrigent, a solubilizing agent, a suspension aid, an emulsifying agent, a coating agent, or combinations thereof.

It should be understood that the pharmaceutical compositions of the present disclosure can further include additional known therapeutic agents, drugs, modifications of the synthetic compounds into prodrugs, and the like for alleviating, mediating, preventing, and treating the diseases, disorders, and conditions described herein.

The pharmaceutical compositions including the TRPV4 agonist and pharmaceutical carriers used in the methods of the present disclosure can be administered to a subset of individuals in need. As used herein, an "individual in need" refers to an individual at risk for or having elevated intraocular pressure. Additionally, an "individual in need" is also used herein to refer to an individual at risk for or diagnosed by a medical professional as having glaucoma. As such, in some embodiments, the methods disclosed herein are directed to a subset of the general population such that, in these embodiments, not all of the general population may benefit from the methods. Based on the foregoing, because some of the method embodiments of the present disclosure are directed to specific subsets or subclasses of identified individuals (that is, the subset or subclass of individuals "in need" of assistance in addressing one or more specific conditions noted herein), not all individuals will fall within the subset or subclass of individuals as described herein. In particular the individual in need is a human. The individual in need can also be, for example, a research animal such as, for example, a non-human primate, a mouse, a rat, a rabbit, a cow, a pig, and other types of research animals known to those skilled in the art.

The disclosure will be more fully understood upon consideration of the following non-limiting Examples.

EXAMPLES

Materials and Methods

Reagents

TRPV4 agonist (GSK 1016790A), or antagonist (HC 067047) were obtained from Sigma (St. Louis, Mo.) and TOCRIS (Bristol, UK), respectively. Acetylated α-tubulin, anti-β actin, anti-γ tubulin monoclonal antibodies were purchased from Sigma (St. Louis, Mo.). Anti-TRPV4 polyclonal antibody was from Alomone Lab (Jerusalem, Israel). Anti-adenylate cyclase III antibody was from Santa Cruz Biotech (Santa Cruz, Calif.). Anti-IFT-88 polyclonal antibody was from ProteinTech (Chicago, Ill.). β-catenin and pericentrin antibodies were obtained from PW Majerus (Washington University, St. Louis). The anti-FLAG-M2 antibody was purchased from Agilent (Englewood, Colo.). Anti-FLAG beads were obtained from Clontech (Mountain View, Calif.). Secondary antibodies AlexaFluor 488 and 594 anti-mouse IgG, Cy3 anti-mouse IgG, HRP-conjugated anti-rabbit and anti-mouse IgG were obtained from Jackson Laboratories (West Grove, Pa.). IRDye anti-mouse and anti-rabbit (680 and 800) were obtained from Li-cor Bioscience (Lincoln, Nebr.). Primers for Gli1, TNFα, and TGFβ and GAPDH were obtained from IDT (Coralville, Iowa).

Animals

All animal experiments followed the guidelines of the ARVO Statement for the Use of Animals in Ophthalmic and Vision Research and were approved by the Institutional Animal Care and Use Committee of Indiana University School of Medicine. Wpk rats, a polycystic kidney disease model, were housed under a 12-hour light/dark cycle with free access to water and food (Smith et al., Nat. Genet. 2006, 38(2):191-196). For topical anesthesia, 50 mg/ml sodium pentobarbital was injected.

Cell Culture and Tissue Isolation

The trabecular meshwork (TM) tissues were isolated from healthy human cadaver eyes by careful dissection, with Indiana University IRB approval. Culture of TM cells was performed according to Tripathi & Tripathi (Exp. Eye Res. 1982, 35(6):611-624). The identity of trabecular meshwork cells was established by morphology and ability to take up acetylated low-density lipoprotein and to secrete tissue plasminogen activator. Human RPE cells (hTERT-RPE1) cell lines were previously described by Luo et al. (Hum. Mol. Genet. 2012, 21(15):3333-3344). NHF588 were obtained from D. Spandau (Indiana University) and HEK293T cells were obtained from J. B Travers (Indiana University).

DNA Plasmid and Transfection

GFP-OCRL-WT and FLAG-OCRL-WT were obtained from Addgene (Cambridge, Mass.). Flag-TRPV4 constructs were gifts from the Lefkowitz lab (Duke University, NC). TRPV4 cDNA was purchased from Thermo Scientific (Pittsburgh, Pa.). OCRL D499A mutant (1661 A>C) was generated using QUIKCHANGEII® kit from Stratagene (Santa Clara, Calif.). Transfections were performed using LIPOFECTAMINE®2000 or Polyethylenimine (PET) according to the manufacturer's protocol (Life Technologies, Grand Island, N.Y.).

Immunofluorescence

For immunofluorescence techniques and cilia measurement, cell culture slides were treated with paraformaldehyde (PFA) for fixation for 10 minutes at room temperature (RT) followed by permeabilization with 0.5% Triton X-100. Samples were then blocked with phosphate-buffered saline (PBS)/0.5% bovine serum albumin (BSA)/10% normal goat serum (NGS) for 30 minutes at RT. Primary antibodies were applied at 4° C. overnight, followed by secondary antibodies at RT for 1 hour. Imaging for cilia measurements was performed with a Zeiss LSM700 as described by Luo et al. (Hum. Mol. Genet. 2012. 21(15):3333-3344).

Immunoprecipitation

Co-immunoprecipitation experiments were performed as described (Kang et al., Invest. Ophthalmol. Vis. Sci. 2013, 54(4):2523-2532). Briefly, HEK293T cells were lysed in phosphate buffered saline followed by incubation with the anti-FLAG beads for 3 hours at 4° C. The protein-antibody complexes were then washed with lysis buffer, resolved by SDS-PAGE and subjected to immunoblot analysis.

Immunoblot Analysis

Cell lysates were subjected to SDS-PAGE. Equal amounts of protein were run on 10-12% gel and transferred to nitrocellulose membrane (BioRad, Hercules, Calif.). Membranes were blocked in 5% non-fat dried milk in PBS. Primary and secondary antibodies were diluted in the concentrations described in Luo et al. (Hum. Mol. Genet. 2012, 21(15):3333-3344). An Odyssey Imaging system (Li-Cor Bioscience) was used to analyze the immunoblots.

Quantitative Real-Time PCR

Total RNA was extracted using the RNAEASY® kit (Qiagen). Purified RNA was quantitated with the NANODROP® 2000 (Thermo Fisher Scientific, Lafayette, Colo.). Reverse transcription of total RNA was done using SUPERSCRIPT cDNA synthesis kit (Invitrogen) with random hexamers. Quantitative RT-PCR was performed using the RQ and ΔΔCt method on a Step One Real-Time PCR machine (Bio-Rad Laboratories, Hercules, Calif.). Each assay was performed in triplicate with Power SYBR green MasterMix (SA Biosciences, Frederick, Md.).

Measurement of Intraocular Pressure

Intraocular Pressure (IOP) was measured with the TONO-LAB tonometer TV02 (Helsinki, Finland) with rats under topical anesthesia. IOP was measured using six valid rebound measurements of the device from the eye, where the mean of the middle five readings was taken for one summary measurement. A single set of readings was collected with the best reproducibility indicator during the IOP measurements.

Hydrostatic Pressure Chamber

To analyze the cellular changes in the TM cells, a hydrostatic pressure chamber was developed similar to that of Mandel et al. (Invest. Ophthalmol. Vis. Sci. 2010, 51(6): 3129-3138). The cells were grown in 60 mm polycarbonate dishes sealed to attach to a plastic column filled with 400 mL DMEM/F12 media with or without serum for cilia induction. The column was temperature controlled at 37° C. in humidified chamber. The height of the column was set at 67 cm for a pressure at the base of 50 mmHg; 40 cm fluid column for a pressure of 30 mmHg at the base (Mandel et al., Invest. Ophthalmol. Vis. Sci. 2010, 51(6):3129-3138). Pressure at the base of the column was verified by TONOPEN® (Reichert, Depew, N.Y.).

$Ca^{2+}$ Imaging

Flow-induced $Ca^{2+}$ signals were examined in the presence and absence of cilia in HTM cells. To remove primary cilia, 2 mM aqueous chlorohydrate (Sigma, St. Louis) was added for 48 hours. Prior to flow experiments, cells were washed three times with PBS, and fresh medium was added for 24 hours. The Fura-2 loaded HTM cells were subjected to laminar flow rates as indicated. Single-cell analysis of the $Ca^{2+}$ signals (ratio 340/380 nm) of the same experiment was obtained. Intracellular $Ca^{2+}$ changes were monitored by ratiometric imaging of Fura-2 AM fluorescence in the HTM cells. HTM cells were loaded with Fura-2 AM for 1 hour at 37° C. in PBS with 40 µM fura-2 AM, 0.33 mM pyruvate, 0.901 mM $Ca^{2+}$, 0.5 mM $Mg^{2+}$, 5.5 mM glucose, and 0.1% BSA. The Fura-2 AM-loaded HTM cells were washed in PBS and were mounted in the chamber. $Ca^{2+}$ imaging experiments were performed using a monochromator-based TILL PHOTONICS imaging system, which was attached to an inverted ZEISS microscope equipped (×2.5 objective) with a back-illuminated ANDOR CCD camera. Fura-2 AM was alternately excited at 345 nm and 380 nm and the emitted light was collected using a 510-nm long-pass filter.

The TILLVISION software (TILL PHOTONICS) was used to acquire all fluorescence imaging experiments and to perform the analysis of images. Images were acquired every 2 seconds. The background fluorescence was subtracted and the intracellular $Ca^{2+}$ concentration ($[Ca^{2+}]i$) was calculated using the equation: $[Ca^{2+}]i=Kd\times[(R-Rmin)/(Rmax-R)]\times[Fmax(380)/Fmin(380)]$ (R is the fluorescence ratio, Rmax is the ratio at saturation calcium concentration, Rmin is the ratio at zero calcium in the medium, Fmin(380) is the fluorescence at 380 nm at zero $Ca^{2+}$ concentration in the medium, and Fmax(380) is the fluorescence at 380 nm at saturation $Ca^{2+}$ concentration) (Touw et al., Am. J. Physiol. Gastro. Liver Physiology 2012, 302(1):G66-76).

Electron Microscopy

With an IRB approved study by Indiana University, human trabecular tissues were obtained at the time of trabeculectomy and immediately placed in 2.5% Glutaraldehyde, 2% paraformaldehyde in 0.1 M Na Cacodylate, pH 7.4. Images were obtained as described in Blitzer et al. (Proc. Natl. Acad. Sci. USA 2011, 108(7):2819-2824).

Lowe Syndrome Keratinocytes

A keratinocyte cell line was established from an 8-year old male patient previously diagnosed with Lowe syndrome with bilateral congenital glaucoma and cataracts at Riley Children's Hospital, Indianapolis, Ind. after informed consent was obtained from the patient's parents and in accordance with an IRB approved study by Indiana University. At 12-hours after birth, the patient was identified as having bilateral elevated pressure, opaque corneas, and cataracts. Two weeks after delivery the patient underwent left eye trabeculotomy and trabeculectomy surgeries for glaucoma, followed by the right eye. The patient then had cataract surgery subsequently in both eyes. Urinalysis revealed proteinuria and tissue biopsy confirmed Lowe syndrome. The patient subsequently required multiple eye surgeries for TOP lowering, resulting in counting finger vision in the right eye and hand-motion vision in the left eye.

Patient Mutation Analyses

With IRB approval, patient keratinocyte samples were used for DNA isolation. The 25 coding exons and cDNA ORF of OCRL were amplified under standard conditions and directly sequenced using an ABI 377 DNA sequencer (Applied Biosystems). Mutations were verified in an ethnically matched control individual.

Lowe Syndrome Patient Fibroblasts

Primary fibroblasts (GM01676 and GM03265, referred to as Lowe 1 and Lowe 2, respectively) generated from two Lowe syndrome patients with defects in the OCRL gene were obtained from the Coriell Institute for Medical Research (Camden, N.J.) and previously characterized by Luo et al. (Hum. Mol. Genet. 2012. 21(15):3333-3344) and Coon et al. (Hum. Mol. Genet. 2012, 21(8):1835-1847). GM 01676 cells contain a mutation in the OCRL gene (2479C>T) resulting in a premature stop at codon 827 (R827X).

Statistical Analysis

Results are expressed as mean values±standard deviation (SD). Statistical analysis was performed using student t-tests (SPSS, Chicago, Ill.). A p-value of less than 0.05 was considered statistically significant.

Example 1

In this Example, isolated trabecular meshwork (TM) tissue from the anterior segment of human eyes was analyzed for the presence of cilia by immunofluorescence and electron microscopy.

Trabecular meshwork removed from human donor eyes and surgical TM specimens during glaucoma surgery were immunostained with anti-Arl13b, acetylated α-tubulin (Ac-Tub), γ-tubulin (γ-Tub), and DAPI (to visualize cell nuclei). TM sections of human eyes were fixed, sectioned and electron microscopy performed. TEM images showed basal body and axonemal structures (FIG. 1, arrows).

Figure 2A:
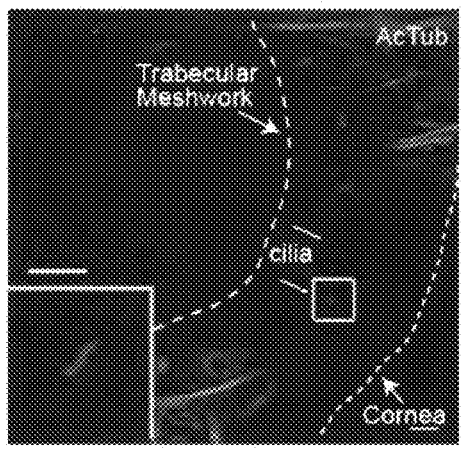
FIG. 2A is an immunofluorescent micrograph of the trabecular meshwork removed from human donor eyes and immunostained with anti-Arl13b (red), anti-acetylated α-tubulin (AcTub, red), anti-γ-tubulin (γ-Tub, green) and DAPI (blue), as discussed in Example 1. Scale bar=5 μm.
Figure 2B:
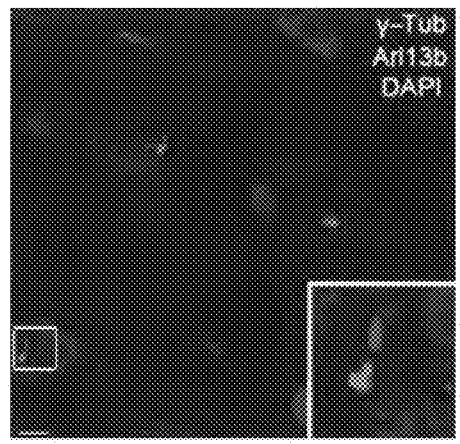
FIG. 2B is an immunofluorescent micrograph of surgical trabecular meshwork specimens obtained during glaucoma surgery and immunostained with anti-Arl13b (red), anti-acetylated α-tubulin (AcTub, red), anti-γ-tubulin (γ-Tub, green) and DAPI (blue), as discussed in Example 1. Scale bar=5 μm.
Figure 2C:
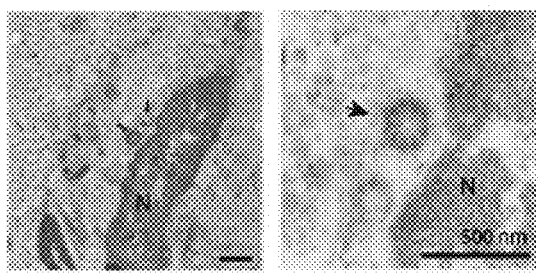
FIG. 2C are transmission electronmicrographs of trabecular meshwork sections of human eyes showing basal body and axonemal structures (indicated with arrows) and the cell nucleus (N), as discussed in Example 1. Scale bar=500 nm.
Figure 2D:
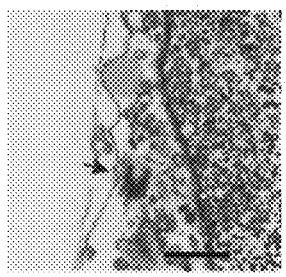
FIG. 2D is a transmission electronmicrograph of trabecular meshwork section of a human eye showing basal body and axonemal structures (indicated with arrows), as discussed in Example 1. Scale bar=500 nm.
Figure 2E:
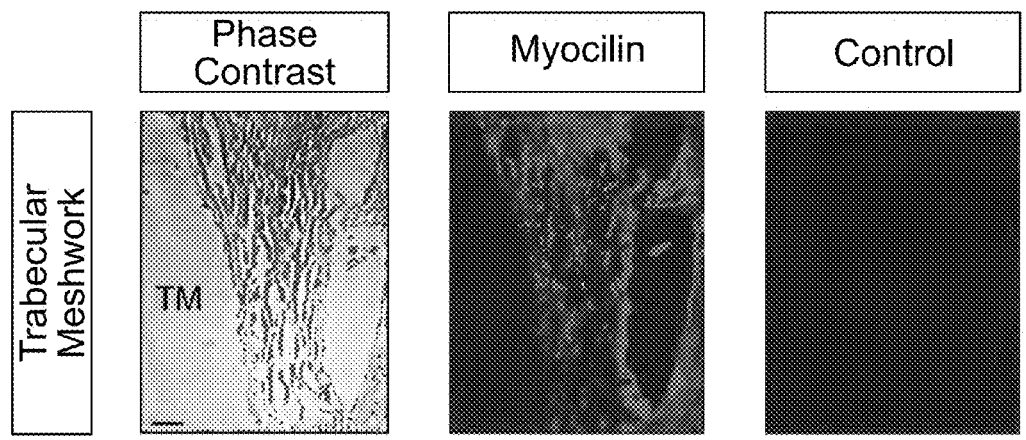
FIG. 2E depicts characterization of human TM tissue. Human trabecular tissues were stained with anti-myocilin antibody (green) and DAPI (blue). Phase-contrast and immunofluorescence images were obtained. (Scale bar, 10 μm).
Figures 2F, 2G, 2H:
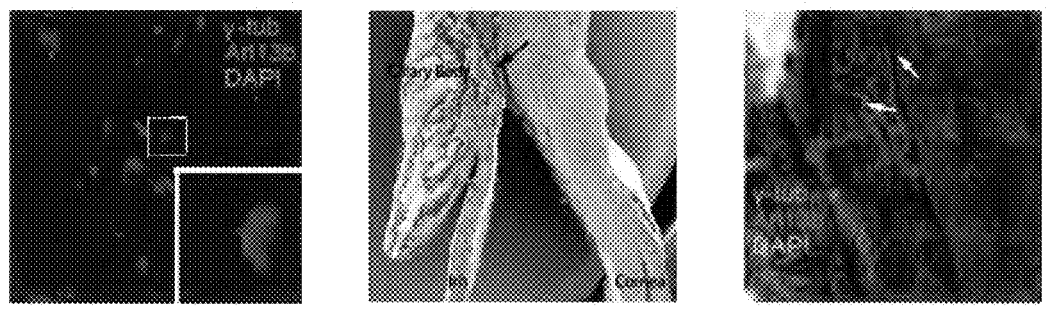
FIG. 2F is a fluorescence micrograph of trabecular meshwork cilia from murine eyes stained with anti-Arl13b (red) anti-γ-tubulin (γ-Tub, green) and DAPI (blue), as discussed in Example 1. Scale bar=5 μm.
FIG. 2G is a high magnification scanning electron micrograph showing trabecular meshwork cilia from porcine eyes, as discussed in Example 1.
FIG. 2H is a low magnification scanning electron micrograph showing trabecular meshwork cilia from porcine eyes, as discussed in Example 1. Scale bar=5 μm.

Trabecular meshwork (TM) tissue from the anterior segment of the eye contains cilia-like structures (see schematic illustration in FIG. 1). As shown in FIGS. 2A and 2B, primary cilia were detected in TM tissues by immunostaining for acetylated α-tubulin or Arl13b, a small GTPase localized in the cilia, while the basal body was detected by staining for γ-tubulin. Collectively, this revealed numerous cilia-like structures in the uveoscleral region of the TM (FIG. 2A). The similar staining of cilia in TM tissues that were removed en face immediately following trabeculectomy from the eyes of glaucoma patients indicated that positive staining was not an artifact of fixation (FIG. 2B). The detection of primary sensory cilia with characteristic "9+0" structures by electron microscopy confirmed their presence in the TM (FIGS. 2C and 2D). Specificity for TM was verified by immunostaining of myocilin, a TM-enriched protein (FIG. 2E). Similar observations were noted in the trabecular meshwork of murine (FIG. 2F), porcine (FIGS. 2G and 2H) and bovine (FIGS. 2I and 2J) eyes. These results demonstrated that primary cilia are present in the TMs of many mammalian species.

Serum starvation is a well-described method for the induction of primary cilia. To determine whether serum starvation could induce the formation of cilia, cultured human trabecular meshwork (HTM) cells were subjected to serum starvation for 48 hours. Following serum starvation, HTM cells were immunostained to detect Arl13b, IFT88 (an intraflagellar transport protein), IFT43, IFT57, adenylate cyclase III (a cilia marker), and γ-tubulin (FIG. 2K).

Figure 3A:
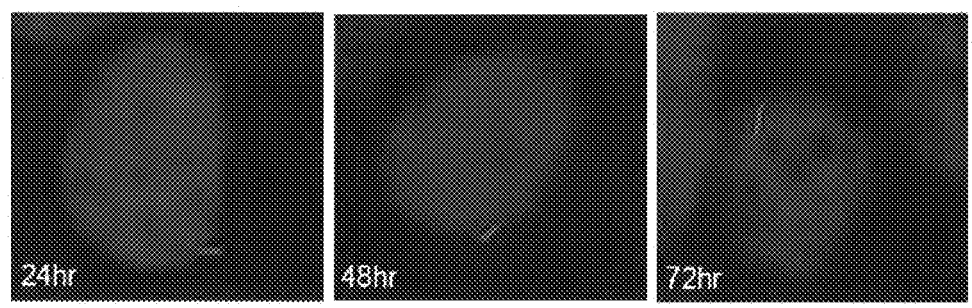
FIG. 3A are fluorescence micrographs showing cilia formation in serum-starved HTM cells for 24 hours, 48 hours and 72 hours stained with anti-acetylated α-tubulin (red) and DAPI (blue), as discussed in Example 1. Scale bar=10 μm.
Figure 3B:
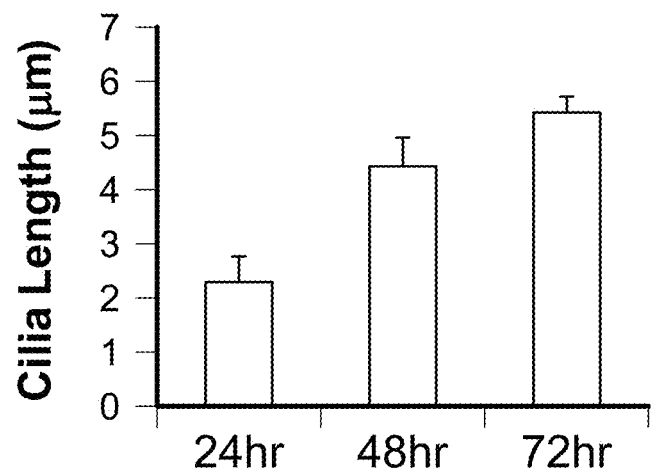
FIG. 3B is a graph illustrating cilia length measurements in serum-starved HTM cells for 24 hours, 48 hours and 72 hours, as discussed in Example 1. Error bars represent standard deviation (SD). N>50 cilia, three independent experiments, ANOVA, *, p<0.001.
Figure 3C:
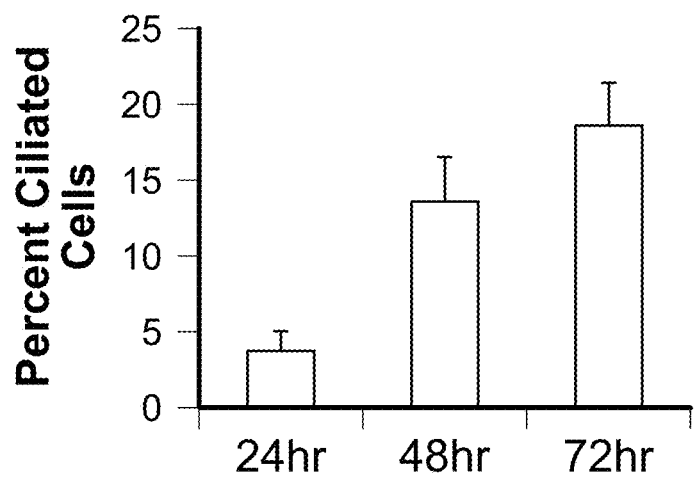
FIG. 3C is a graph illustrating ciliation rate in serum-starved HTM cells for 24 hours, 48 hours and 72 hours, as discussed in Example 1. Error bars represent standard deviation (SD). N>50 cilia, three independent experiments, ANOVA, *, p<0.001.

HTM cells were then serum starved for 24 hours, 48 hours and 72 hours. As visualized in FIG. 3A, cilia length increased over time during serum starvation. Measurements of cilia demonstrated that the average lengths of cilia increased following serum deprivation. At 24 hours the cilia lengths were 2.2±0.7 μm; at 48 hours, 4.3±0.6 μm; and were 5.6±0.4 μm at 72 hours (FIG. 3B). As illustrated in FIG. 3C, ciliation rate also increased over time. These results strongly confirmed the presence of functional primary cilia in trabecular meshwork cells.

Example 2

In this Example, the effect of pressure changes on cilia length in TM cells was determined.

Figure 4A:
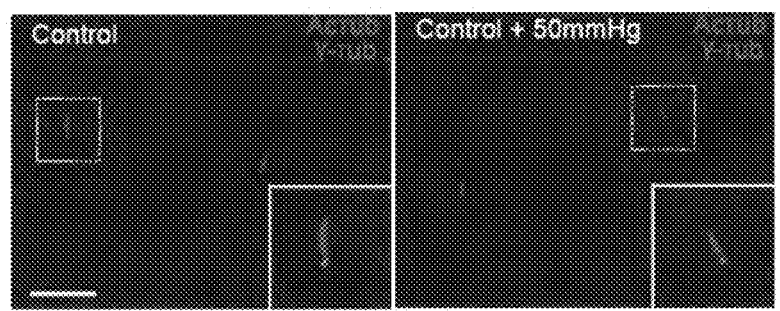
FIG. 4A are fluorescent micrographs of serum-starved HTM cells that were cultured in atmospheric (control, 0 mmHg) and 50 mmHg pressure and immunostained with anti-acetylated α-tubulin (AcTub, red), and anti-γ tubulin (γ-Tub, green). Insets show higher magnification of cilia, as discussed in Example 2. Scale bar=5 μm.
Figure 4B:
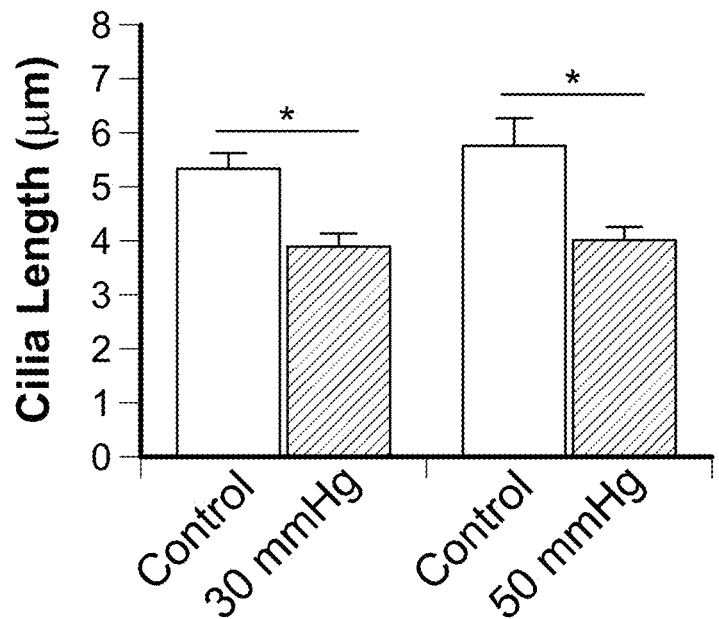
FIG. 4B is a graphical illustration depicting measurements of cilia length of serum-starved HTM cells that were cultured in atmospheric (control, 0 mmHg), 30 mmHg pressure and 50 mmHg pressure from three different experiments, as discussed in Example 2. Error bars represent standard deviation. N>50 cilia; paired t-test *, p value<0.05.
Figure 4C:
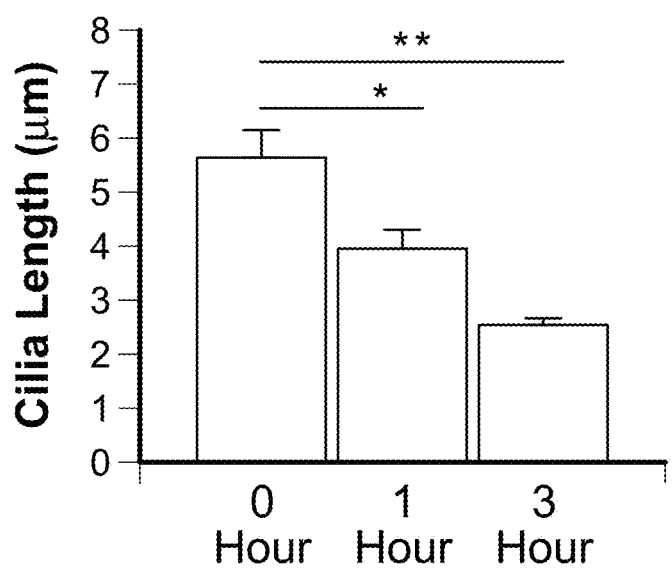
FIG. 4C is a graphical illustration depicting measurements of cilia length of serum-starved HTM cells that were cultured in 50 mmHg pressure for 0 hour, 1 hour and 3 hours and immunostained with anti-acetylated α-tubulin (AcTub, red) to measure cilia length, as discussed in Example 2. Error bars represent standard deviation. N>50 cilia; unpaired t-test *, **p value<0.05, ns—not significant.

HTM cells were serum starved for 48 hours, cultured in a pressure chamber at 0 mmHg, 30 mmHg and 50 mmHg pressure for 0 hour, 1 hour and 3 hours. After cell fixation, cilia were imaged by immunostaining for acetylated α-tubulin. As shown in FIG. 4A, cilia length was reduced by pressure. Average cilia lengths were 5.3±0.2 μm in the normal pressure groups and 3.9±0.2 μm in the high pressure (30 mmHg and 50 mmHg) groups (FIG. 4B). Ciliary length reduction by pressure occurred in a time-dependent fashion (FIG. 4C). Changes in ciliary length were both time- and dose-dependent processes.

TNFα and TGFβ are both highly abundant in the aqueous humor of patients with acute and chronic open angle glaucoma. To determine whether the expression of TNFα was upregulated in response to pressure, its transcript levels were measured by qRT-PCR under different pressures.

HTM cells were serum-starved for 48 hours and treated with saline, saline plus 50 mmHg pressure, chlorohydrate, and chlorohydrate plus 50 mmHg pressure for 3 hours. Levels of mRNA of TNFα, TGFβ1 and Gli1 were then measured. Results presented represent three independent experiments. Serum-starved HTM cells were also placed under 50 mmHg pressure for 0, 10, 20, 40, 60 and 80 minutes and analyzed for expression of TNFα and IL-33. Results presented represent three independent experiments.

Figure 4D:
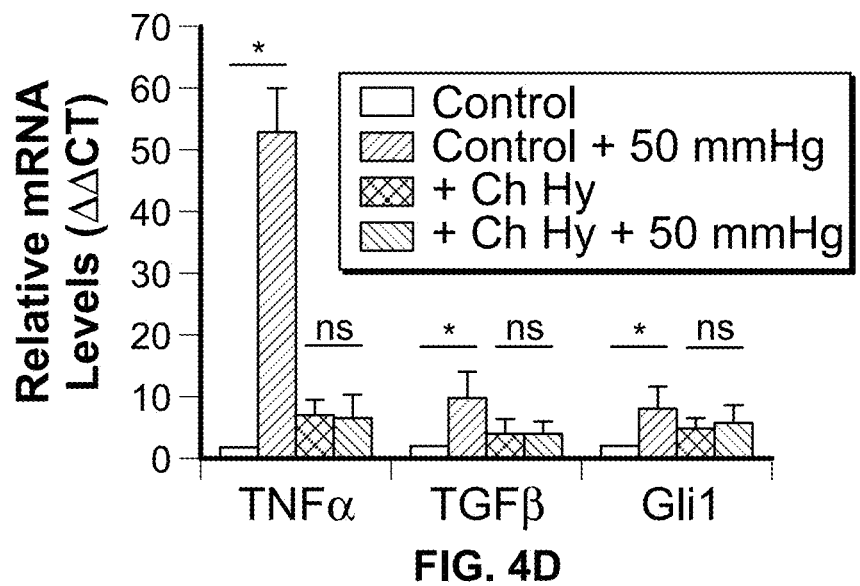
FIG. 4D is a graphical illustration depicting mean mRNA levels of TNFα, Gli1 and TGFβ measured by RT-PCR in serum-starved HTM cells treated with saline (control), saline plus 50 mmHg pressure, chlorohydrate (+CH Hy), and chlorohydrate plus 50 mmHg pressure (+CH Hy+50 mmHg) for 3 hours from three independent experiments, as discussed in Example 2. Error bars represent standard deviation, *t-test p value<0.05, ns—not significant.
Figure 4E:
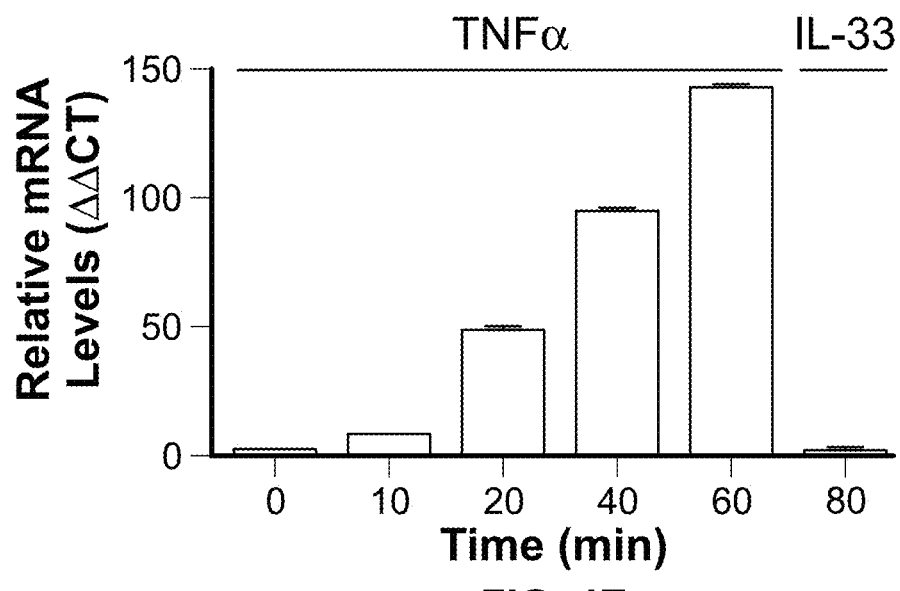
FIG. 4E is a graph illustrating mean relative expression of TNFα mRNA and IL-33 mRNA in serum-starved HTM cells and placed under 50 mmHg pressure for 0, 10, 20, 40, 60 and 80 minutes, as discussed in Example 2. Mean of three independent experiments is shown. Error bars represent SD.

Following 60 minutes of application of 50 mmHg pressure, which mimics acute angle closure glaucoma, a robust elevation of TNFα transcription was observed (FIG. 4D). The lack of changes in IL-33 transcript indicated that the effects on TNFα are specific (FIG. 4E). Further, application of 50 mmHg pressure markedly elevated the transcript levels of TNFα and TGFβ1, but had modest effects on Gli1, a factor in the Sonic Hedgehog pathway that requires primary cilia for signaling (FIG. 4D). The dependence of these effects on functional cilia was then determined by testing their sensitivity to chlorohydrate, which effectively removes cilia. Treatment of cells with chlorohydrate reduced the elevation of gene transcription in response to pressure (FIG. 4D).

Figure 4F:
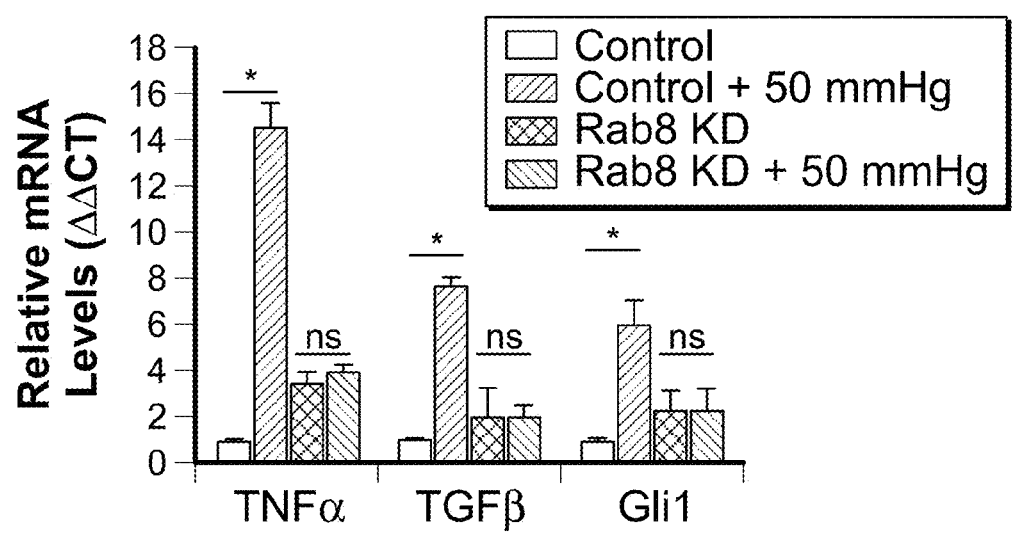
FIG. 4F is a graphical illustration depicting mean mRNA levels of TNFα, Gli1 and TGFβ measured by RT-PCR during cilia formation in serum-starved HTM cells (control) and serum-starved HTM cells (Rab8 knockdown) followed by treatment with saline and saline plus 50 mmHg pressure for 3 hours from three independent experiments, as discussed in Example 2. Error bars represent standard deviation, *p value<0.05, ns—not significant.
Figure 4G:
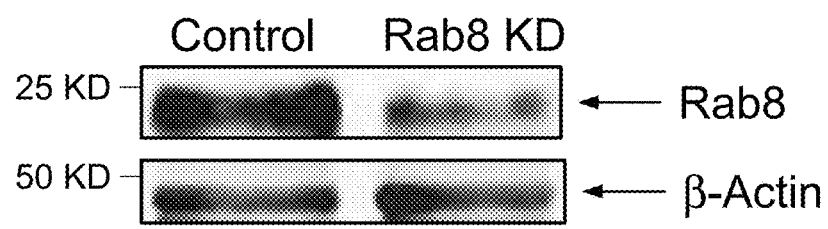
FIG. 4G is an immunoblot for Rab8 level and β-Actin (loading control) level from control KD HTM cell lysates and Rab8 KD HTM cell lysates, as discussed in Example 2.
Figure 4H:
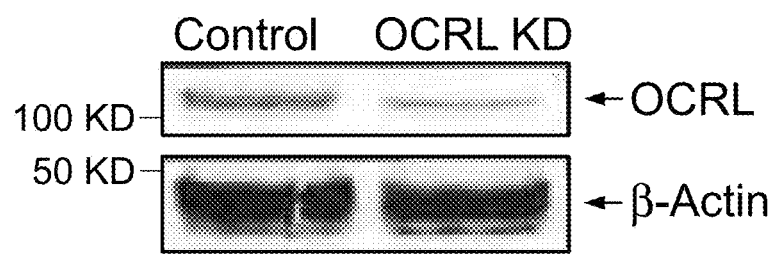
FIG. 4H is an immunoblot for OCRL level and β-Actin (loading control) level from control KD HTM cell lysates and OCRL KD HTM cell lysates, as discussed in Example 2.

In a complementary approach, cilia were ablated by shRNA knockdown of Rab8, which inhibits ciliogenesis. Cells with reduced expression of Rab8 also showed a reduction of gene transcription (Rab8 and OCRL) in response to pressure (FIGS. 4F-4H).

Together, these experiments strongly suggested that enhanced transcription of TNFα and TGFβ1 by pressure occurs via a cilia-dependent process.

Example 3

To further characterize the distribution of ciliary proteins under elevated pressure conditions, intraflagellar transport (IFT) proteins were examined.

Figure 5:
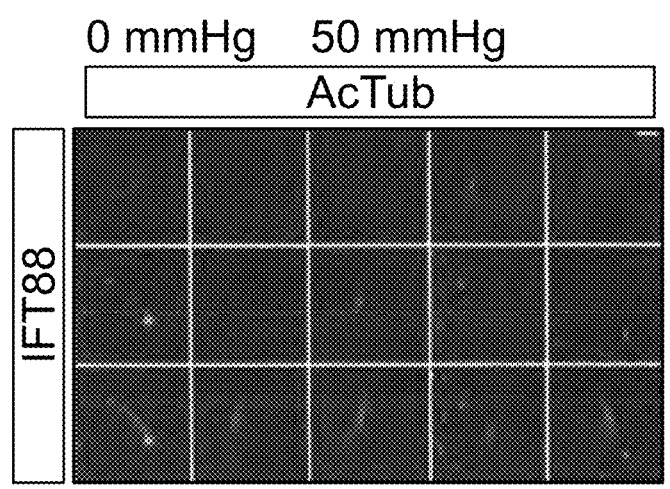
FIG. 5 are fluorescence micrographs of representative images of immunostaining with antibodies for IFT88 (green), acetylated α-tubulin (red), and DAPI (blue), showing the loss of IFT88 in the distal tip of cilia under elevated pressure conditions, as discussed in Example 3. (Scale bar, 10 μm.)
Figure 6:
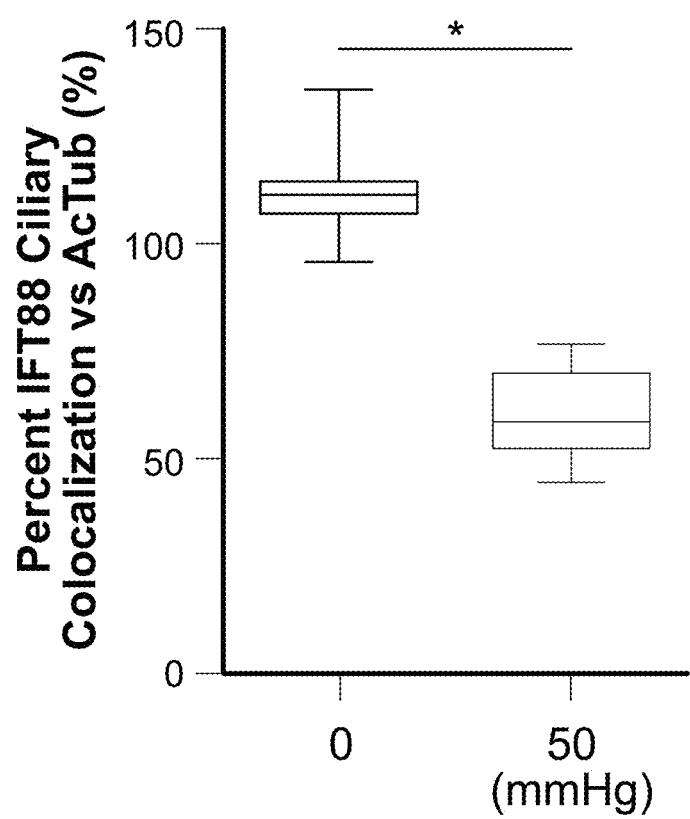
FIG. 6 is a graph showing altered distribution of IFT88 with elevated pressure. HTM cells were serum-starved to induce ciliogenesis, followed by treatment with or without elevated pressure (50 mmHg).

The distribution of proteins involved in both anterograde (IFT57, IFT88) and retrograde (IFT20, IFT43, IFT144) ciliary trafficking were examined using immunohistology. Specifically, HTM cells were serum-starved to induce ciliogenesis, followed by treatment with or without elevated pressure (50 mmHg). Representative images of immunostaining with antibodies for IFT88 (green), acetylated α-tubulin (red), and DAPI (blue) show the loss of IFT88 in the distal tip of cilia under elevated pressure conditions (FIGS. 5 and 6). Only IFT88 was found to have a markedly altered distribution under increased pressure conditions. In control HTM cells, IFT88 distributed to the base as well as to the tip of the axoneme; in HTM cells treated with pressure, IFT88 accumulated at the base of the cilia with a marked decrease at the ciliary tip.

Thus, elevated pressure in cells alter IFT distribution with a resultant change in ciliary protein trafficking.

Example 4

Glaucoma frequently develops after prolonged elevated intraocular pressure (Alward et al., N. Engl. J. Med. 1998, 338(15):1022-1027). Lowe syndrome is a rare X-linked disorder that presents with congenital glaucoma and cataracts, as well as renal dysfunction and CNS abnormalities (Attree et al., Nature 1992, 358(6383):239-242). In this Example, genetic and cellular analysis of a Lowe syndrome patient was conducted.

An 8-year-old male patient with Lowe syndrome who was born with bilateral congenital glaucoma and cataracts was identified. Table 1 summarizes the clinical profile of the patient.

TABLE 1

CLINICAL PROFILE OF LOWE SYNDROME PATIENT

| | Right Eye | Left Eye |
|---|---|---|
| Vision | Counting fingers | Hand motion |
| Intraocular pressure | 40 mmhg | 55 mmhg |
| Axial length | 20.74 | 20.49 |
| Diagnosis | Cataract (discoid) glaucoma | Cataract (discoid) glaucoma Band keratopathy |
| Surgeries | Lensectomy Trabeculectomy trabeculotomy | Lensectomy Trabeculectomy Trabeculotomy Ahmed shunt valve Ecp |

Figure 7:
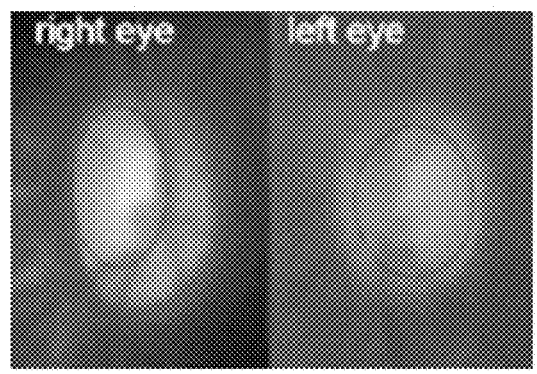
FIG. 7 is a photograph of the optic nerve of a patient with congenital glaucoma and cataracts depicting glaucomatous optic nerve cupping (as indicated by dashed line), as discussed in Example 4.

Less than 12 hours postpartum, the patient was noted to have corneal edema and elevated pressures in both eyes and increased optic nerve cupping (FIG. 7, cup represented by dashed line). The patient subsequently underwent multiple surgeries for glaucoma including trabeculectomy and trabeculotomy with poorly controlled disease.

Figure 8A:
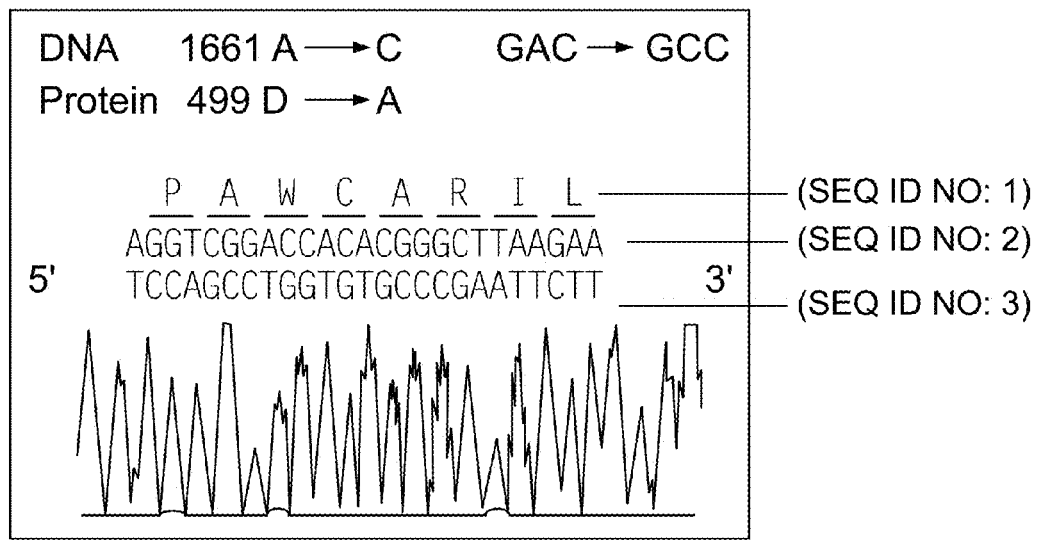
FIG. 8A is a graphical illustration showing the 1661 A>C DNA mutation (D499A amino acid mutation) identified by sequencing PCR products from keratinocytes of a Lowe 3 affected patient, as discussed in Example 4.
Figure 8B:
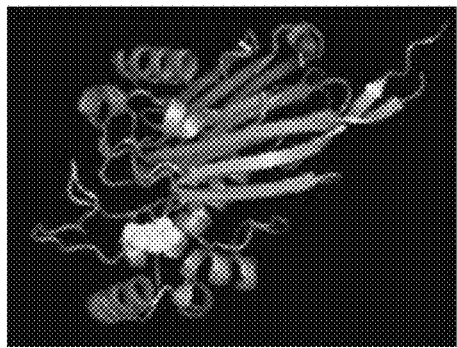
FIG. 8B is an illustration depicting the protein structure of the OCRL 5-phosphatase domain showing the site of mutation, as discussed in Example 4.

DNA sequencing revealed a novel missense mutation in the region encoding the 5-phosphatase domain of the OCRL gene (c.1661 A>C; p.D499A) (FIG. 8A). A model of the OCRL structure was generated by PyMol, ID: 3MTC.pdb. Based on its position in the OCRL structure, this aspartic acid residue was predicted to affect the 5-phosphatase activity of OCRL (FIG. 8B).

Figure 8C:
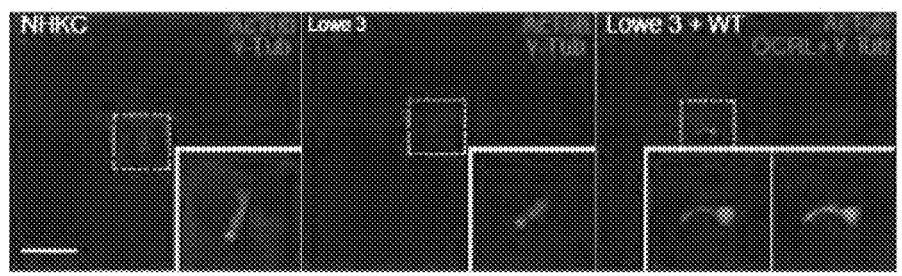
FIG. 8C are fluorescence micrographs of cilia formation in serum-starved keratinocytes from normal control (NHKC), keratinocytes from a Lowe syndrome patient (Lowe 3) and keratinocytes from a patient transduced with WT-GFP-OCRL (Lowe 3+WT) that were stained with anti-acetylated α-tubulin, as discussed in Example 4. Scale bar=10 μm.
Figure 8D:
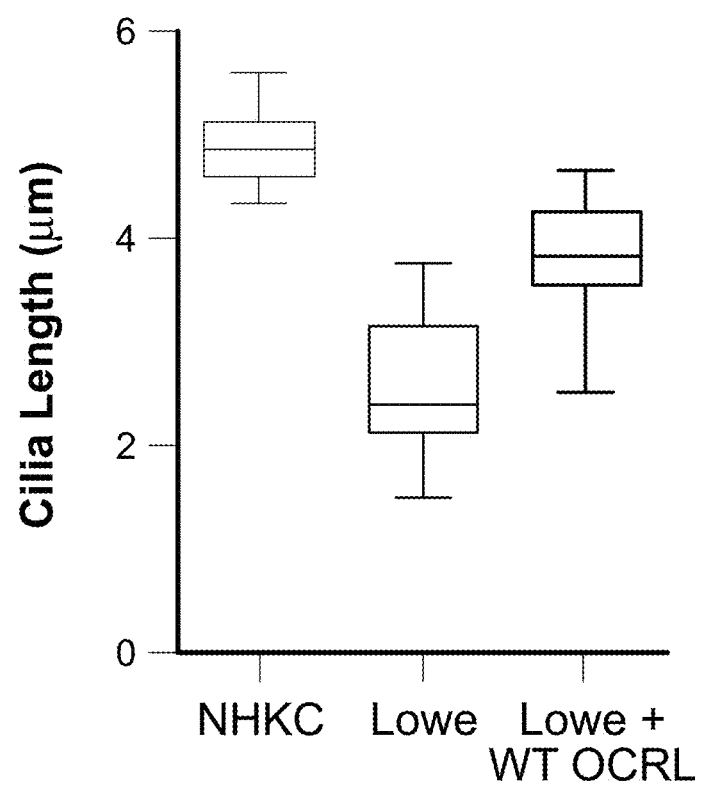
FIG. 8D is a graph illustrating cilia lengths from three independent experiments of cells described in FIG. 3C, as described in Example 3. N=50 cilia, ANOVA, P<0.001.

To further assess the role of OCRL in cilia, the localization of OCRL was visualized in human TM cells following serum starvation. Normal control (NHKC), Lowe syndrome patient (Lowe 3) and patient transduced with WT-GFP-OCRL (Lowe 3+WT) keratinocytes were serum starved for 48 hours and stained for acetylated α-tubulin and γ-tubulin. Immunofluorescence showed that OCRL was concentrated in the axoneme or the membrane of the primary cilium (FIG. 8C). Consistent with OCRL functioning in the cilia of retinal pigment epithelial (RPE) cells, the cilia in keratinocytes derived from this patient were defective. For instance, following serum-starvation, these cells had shortened cilia versus keratinocytes obtained from a healthy individual (FIG. 8D). Upon re-introduction of wildtype OCRL (Lowe 3+WT OCRL), the shortened cilia phenotype was rescued.

Figure 8E:
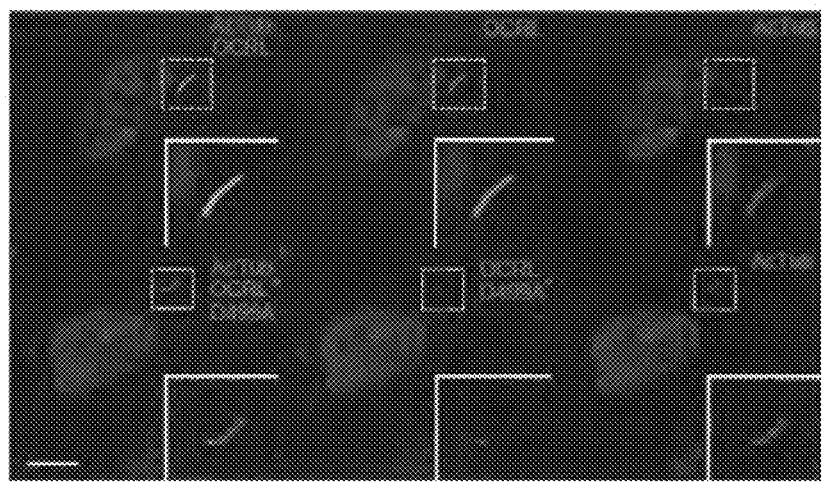
FIG. 8E are fluorescence micrographs of serum-starved HTM cells transfected with GFP-WT OCRL and GFP-D499A-OCRL that were stained with anti-acetylated α-tubulin, as discussed in Example 4. Scale bar=5 μm.
Figure 8F:
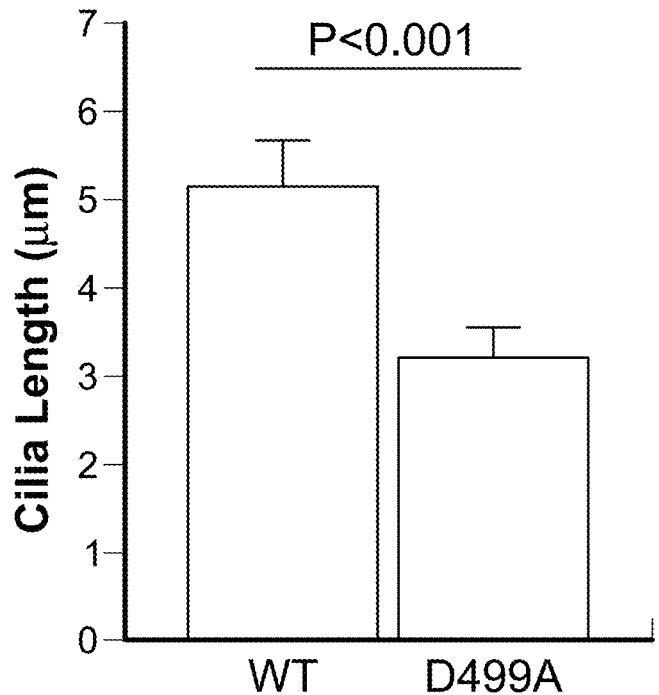
FIG. 8F is a graph illustrating cilia length measurements from serum-starved HTM cells transfected with GFP-WT OCRL and GFP-D499A-OCRL, as discussed in Example 4. Error bars represent SD. N>50 cilia, three independent experiments, unpaired t-test.
Figure 8G:
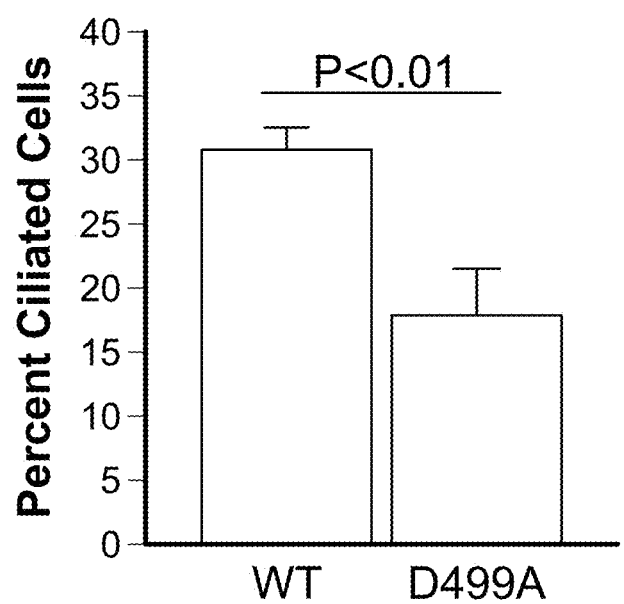
FIG. 8G is a graph illustrating ciliation percent measurements from serum-starved HTM cells transfected with GFP-WT OCRL and GFP-D499A-OCRL, as discussed in Example 4. Error bars represent SD. N>50 cilia, three independent experiments, unpaired t-test.

OCRL mutant cDNA (OCRL D499A) was expressed in HTM cells to determine its effect on cilia formation. Expression of OCRL mutant cDNA resulted in the formation of significantly shorter cilia structures in these cells upon serum-starvation as compared to control cells (FIGS. 8E-8G).

These data implicate OCRL in cilia formation in TM cells, which in turn, is likely required for pressure sensing in the eye.

Given the potential role of OCRL in pressure sensing, the requirement for OCRL for the activation of transcription in HTM cells in response to pressure was assessed.

Figure 8H:
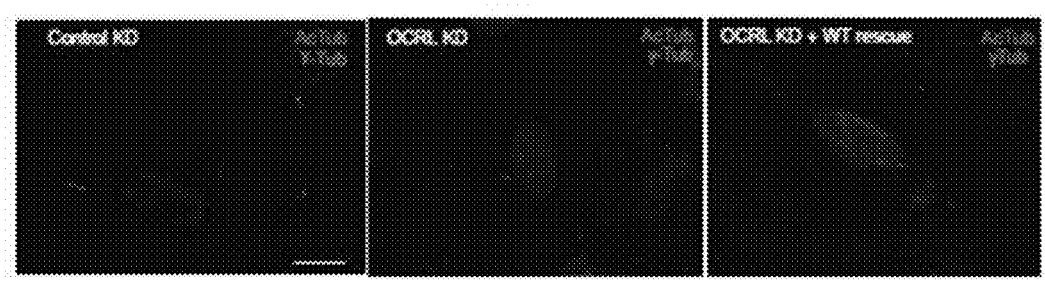
FIG. 8H are fluorescence micrographs of serum-starved control HTM (Control KD), OCRL KD HTM (OCRL KD) and OCRL-WT expressing (OCRL KD+WT rescue) OCRL KD HTM cells incubated with or without 50 mmHg pressure for 3 hours, as discussed in Example 4. Representative photomicrographs showed short cilia in HTM cells with 50 mmHg and OCRL KD HTM cells. Scale bar 5 μm.
Figure 8I:
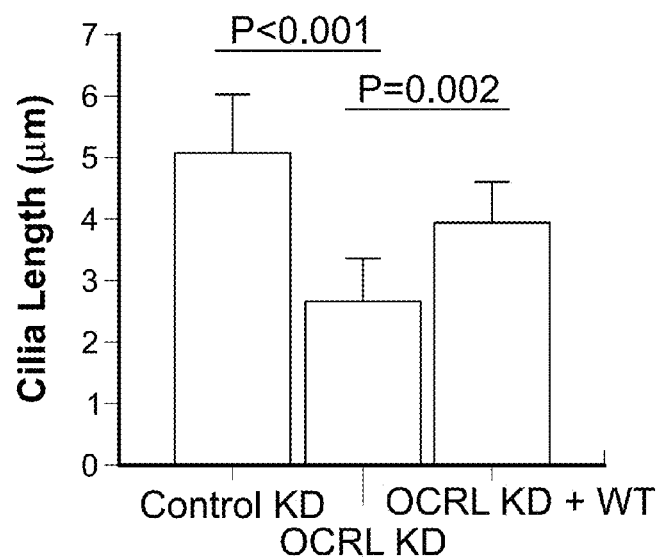
FIG. 8I is a graph illustrating cilia length measurements from serum-starved control HTM (Control KD), OCRL KD HTM (OCRL KD) and OCRL-WT expressing (OCRL KD+WT rescue) OCRL KD HTM cells incubated with or without 50 mmHg pressure for 3 hours, as discussed in Example 4. Error bars represent SD. N>50 cilia, three independent experiments, unpaired t-test.
Figure 8J:
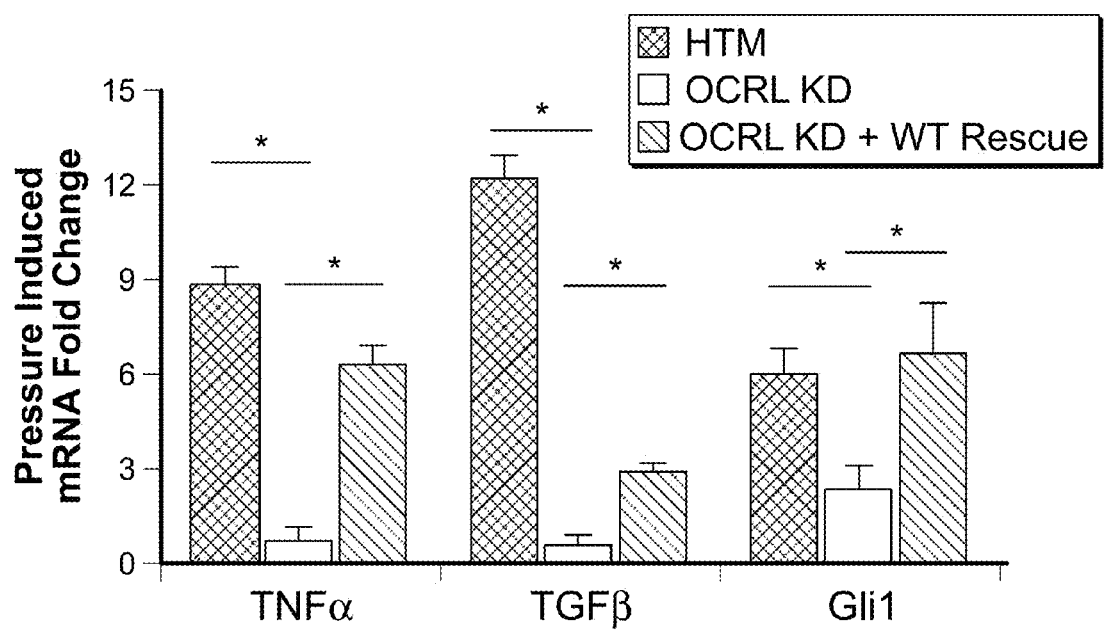
FIG. 8J is a graph illustrating pressure induced TNFα, TGFβ and Gli1 mRNA levels in serum-starved control HTM (HTM), OCRL KD HTM (OCRL KD) and OCRL-WT expressing OCRL KD HTM (OCRL KD+WT rescue) cells incubated with or without 50 mmHg pressure for 3 hours followed by RT-PCR, as discussed in Example 4. Error bars represent standard deviation, paired t-test, P<0.001.

The expression of OCRL was silenced in HTM cells with lentiviral shRNA. Ciliogenesis was then induced by serum starvation, followed by pressure stimulation (see, FIG. 4H and FIGS. 8H and 8I). Cells with reduced OCRL exhibited a significant loss of pressure-dependent TGFβ, TNFα, and Gli1 transcriptional activity, which was restored by re-expression of wildtype OCRL (FIG. 8J).

In a separate approach, pressure-dependent transcription of TGFβ was assessed in primary fibroblasts obtained from wild-type control (NHF558 cells) versus primary fibroblasts from two Lowe syndrome patients with nonfunctional OCRL protein (described in Luo et al., Hum. Mol. Genet. 2012, 21(15):3333-3344). NHF558, Lowe 1 and Lowe 2 fibroblasts, and OCRL-WT expressing Lowe 1 and Lowe 2 fibroblasts were serum starved for 48 hours and incubated with or without 50 mmHg pressure for 3 hours. TGFβ mRNA level was determined by RT-PCR. Pressure-induced TGFβ mRNA levels, measured as a ratio of 50 mmHg fold change over control averaged over three independent experiments is shown (FIG. 8K).

Figure 8K:
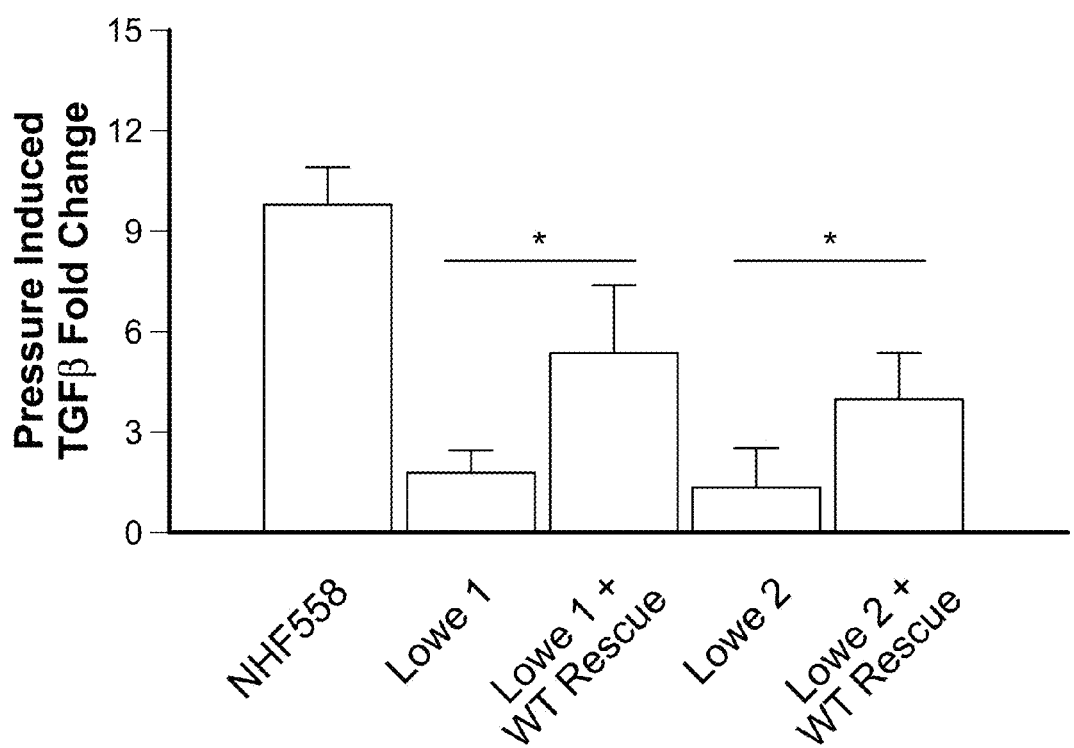
FIG. 8K is a graph illustrating pressure induced TGFβ mRNA level in serum-starved NHF558 fibroblasts, Lowe 1 or Lowe 2 fibroblasts and OCRL-WT expressing Lowe 1 (Lowe 1+WT rescue) or Lowe 2 (Lowe 2+WT rescue) fibroblasts incubated with or without 50 mmHg pressure for 3 hr followed by RT-PCR, as discussed in Example 4. Error bars represent standard deviation, paired t-test, P<0.001.

The levels of TGFβ transcript modestly increased following elevated pressure in mutant cells whereas cells expressing wildtype OCRL showed dramatically increased elevation of TGFβ in response to pressure (FIG. 8K). This further supports the assertion that pressure activates the transcription of TNFα and TGFβ in a manner that requires cilia, which in turn are dependent on functional OCRL.

Example 5

Transient receptor potential vanilloid 4 (TRPV4) is a mechanosensitive calcium permeable cation channel that localizes to cilia where it functions in osmotic regulation. TRPV4 dysregulation has been implicated in diseases with fluid overload, such as hydrocephalus and heart failure. In this Example, the role of TRPV4 in TM cilia and responding to mechanosensory signals was determined.

HTM cells were serum starved for 48 hours and immunostained with anti-TRPV4 and anti-acetylated α-tubulin antibodies. Nuclei were visualized by DAPI staining. Additionally, HEK293 cells were transfected with FLAG-TRPV4, GFP-OCRL, and GFP alone. Immunoblots for OCRL (IB:OCRL) and FLAG-TRPV4 were performed after immunoprecipitation for FLAG.

Figure 9A:
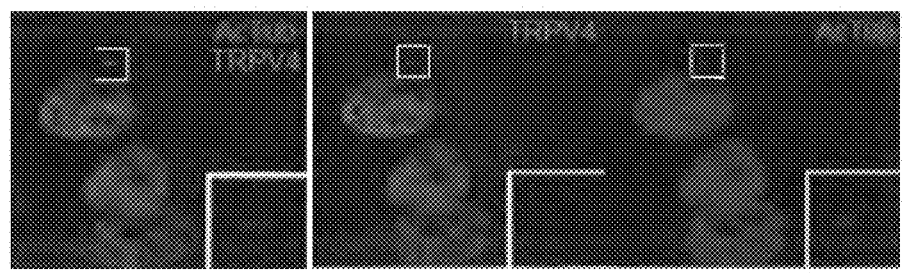
FIG. 9A are fluorescence micrographs of serum-starved HTM cells stained with anti-TRPV4 (green), anti-acetylated α-tubulin (red) and DAPI (blue), as discussed in Example 5. Scale bar=5 μm.
Figure 9B:
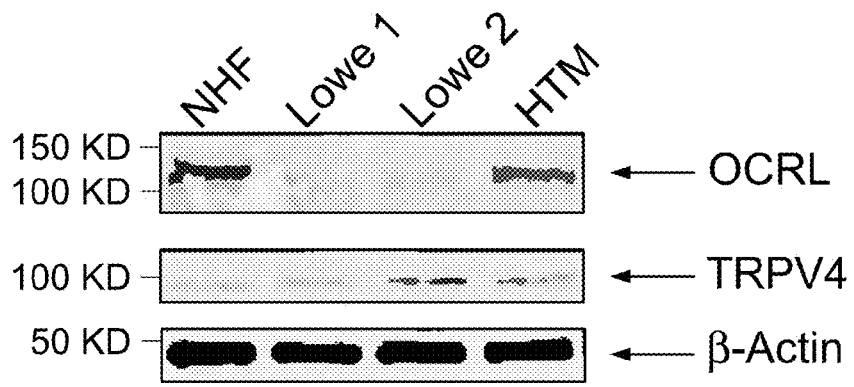
FIG. 9B is an immunoblot for OCRL and TRPV4 levels (β-Actin loading control) from NHF cell lysates, Lowe 1 cell lysates, Lowe 2 cell lysates, and HTM cell lysates, as discussed in Example 5.
Figure 9C:
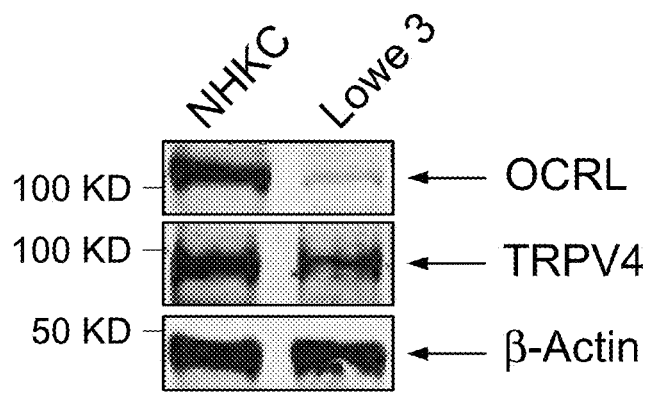
FIG. 9C is an immunoblot for OCRL and TRPV4 levels (β-Actin loading control) from NHKC cell lysates and Lowe 3 cell lysates, as discussed in Example 5.
Figure 9D:
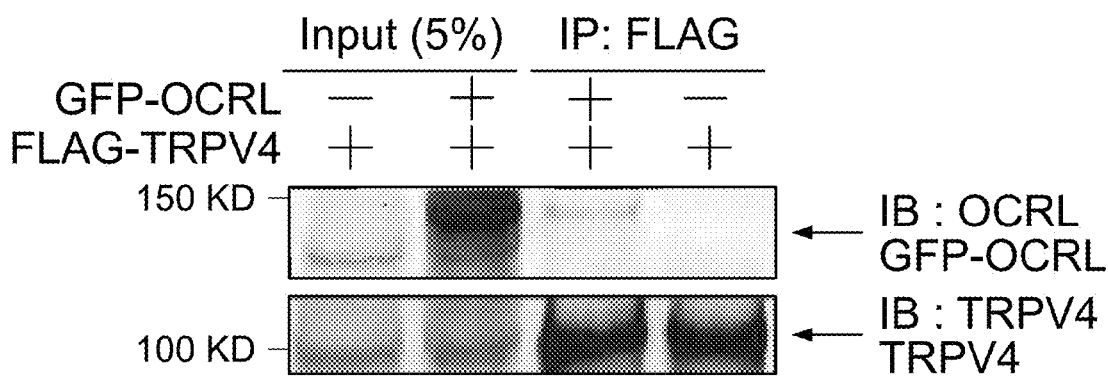
FIG. 9D is an immunoblot (IB) performed after immunoprecipitation of FLAG detecting OCRL and FLAG-TRPV4 in HEK293 cells transfected with FLAG-TRPV4, GFP-OCRL and GFP alone, as discussed in Example 5.
Figure 9E:
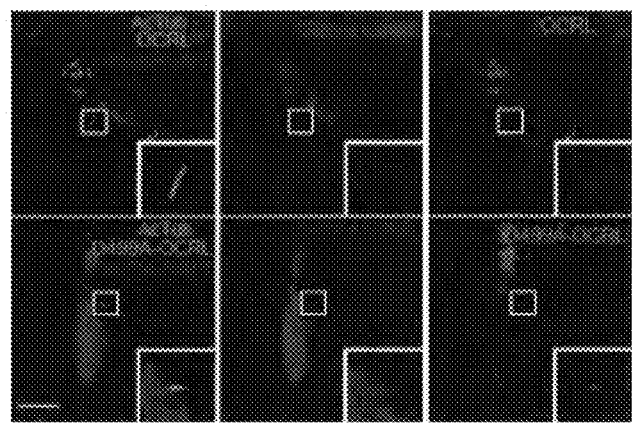
FIG. 9E are fluorescence micrographs of serum-starved HTM cells transfected with FLAG-TRPV4, GFP-OCRL and GFP-D499A-OCRL stained with anti-acetylated α-tubulin (red) and anti-FLAG, as discussed in Example 5. OCRL and D499A are shown in green; FLAG-TRPV4 and DAPI are shown in blue. Scale bar=5 μm.

As shown in FIGS. 9A and 9E, both OCRL and TRPV4 were expressed in HTM cells and co-localized in the primary cilia as indicated by staining for acetylated tubulin. TRPV4 expression was similar in Lowe patient fibroblasts and normal fibroblasts (FIGS. 9B and 9C). Consistent with their colocalization, exogenously expressed TRPV4 specifically co-immunoprecipitated with OCRL (FIG. 9D).

To determine if the D499A OCRL mutant has altered localization and interaction with TRPV4, the localization and interaction with TRPV4 of wildtype OCRL or mutant D499A OCRL in TM cells was determined. HTM cells were serum starved and transfected with FLAG-TRPV4, GFP-OCRL and GFP-D499A-OCRL, followed by immunostaining with anti-acetylated α-tubulin and anti-FLAG antibodies. Nuclei were visualized by DAPI staining. Immunoblots for OCRL and FLAG-TRPV4 after immunoprecipitation was performed on HEK293 cells transfected with FLAG-TRPV4, GFP-OCRL and GFP-D499A-OCRL.

Figure 9F:
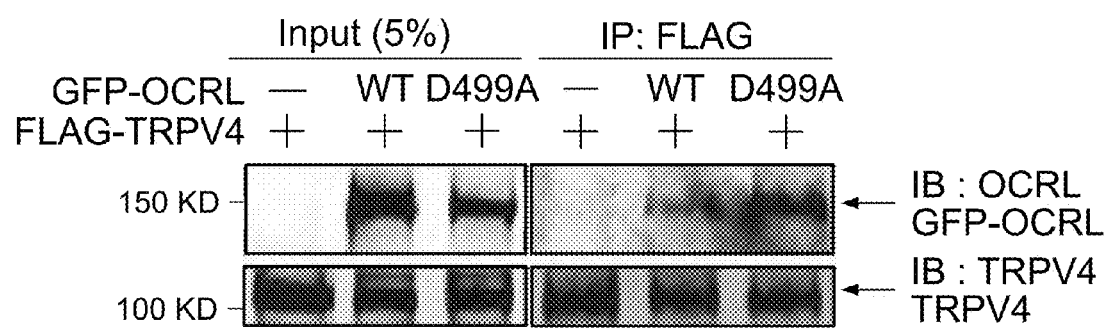
FIG. 9F is an immunoblot (IB) performed after immunoprecipitation of FLAG detecting OCRL and FLAG-TRPV4 in HEK293 cells transfected with FLAG-TRPV4, GFP-OCRL and GFP-D499A-OCRL, as discussed in Example 5.

While TRPV4 localized in the primary cilia in cells expressing wild-type OCRL, its localization to cilia was markedly diminished in cells expressing the D499A OCRL mutant (FIG. 9E). The D499A OCRL mutant immunoprecipitated with TRPV4 to a much greater degree than with wildtype OCRL (FIG. 9F). These results demonstrate that the D499A has a dominant-negative effect of sequestering TRPV4 out of the cilia.

Figure 10A:
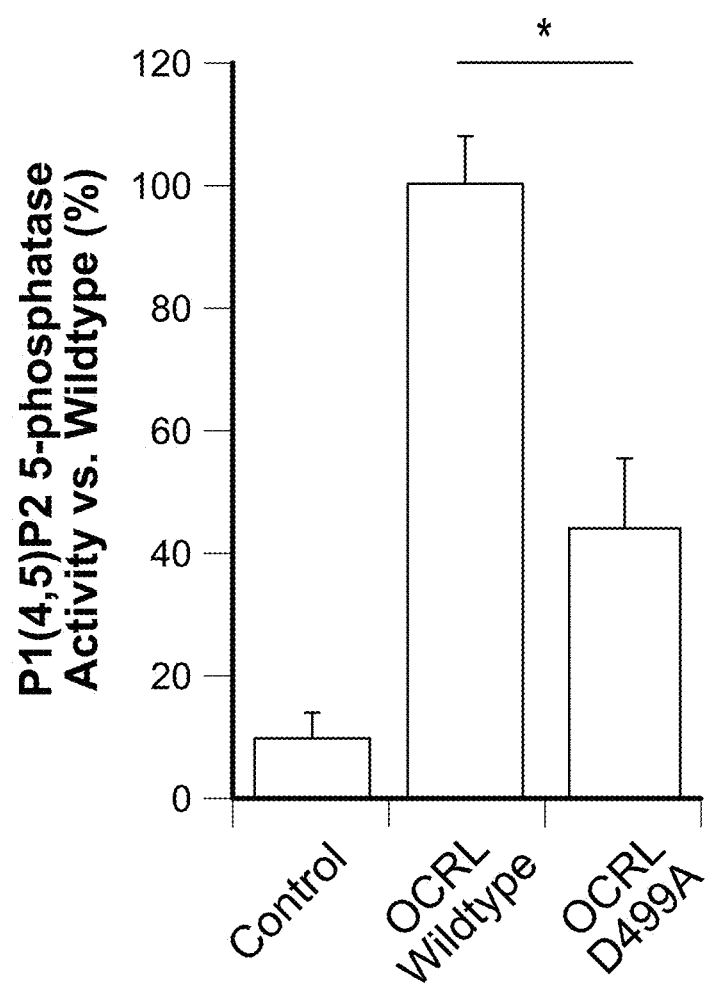
FIG. 10A is a graph depicting that OCRL D499A mutant exhibited decreased PI(4,5)P2 5-phosphatase activity. HTM cells transfected with FLAG-alone, FLAG-OCRL-WT, or FLAG-OCRL-D499A, immunoprecipitated with anti-FLAG beads and subjected to PI(4,5)P2 5-phosphatase assay. Enzymatic activity is indicated as a ratio with the wild-type OCRL; average of three independent experiments is shown. Error bars represent SD. Paired t test, *P<0.05
Figure 10B:
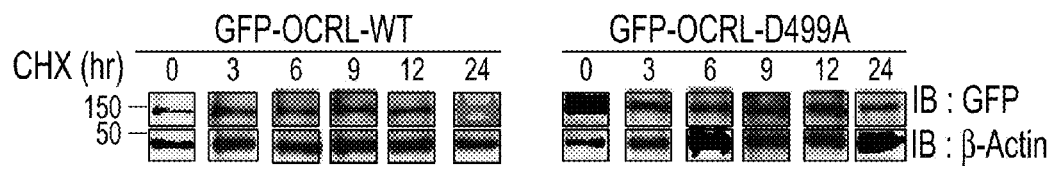
FIGS. 10B and 10C depict that OCRL-WT and D499A mutant exhibited similar half-life for protein stability. The levels of GFP-OCRL-WT, GFP-OCRL-D499A, and endogenous β-actin were detected by immunoblot of lysates from HEK293T cells transfected with GFP-OCRL-WT or GFP-OCRL-D499A following treatment for the indicated times with CHX (200 μg/mL). A graph is shown of the ratios of GFP-OCRL to β-actin and the resulting half-lives (t1/2) in cells expressing GFP-OCRL-WT or GFP-OCRL-D499A (FIG. 10C).
Figure 10C:
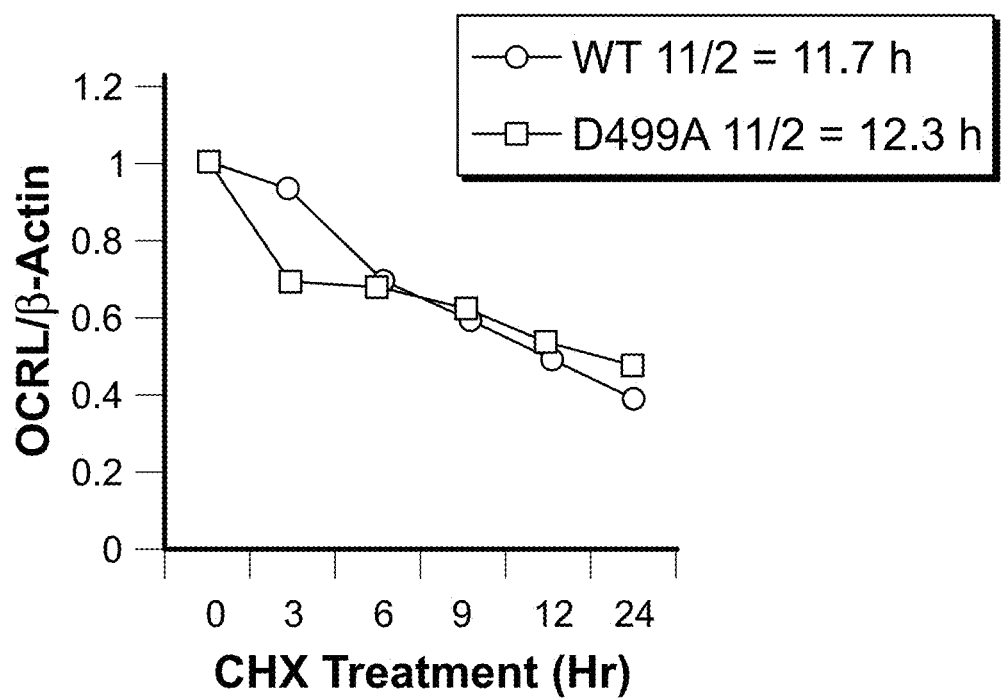

Further, the function of the OCRL D499A mutant was assessed in vitro, and it was found that the enzymatic activity of PI(4,5)P2 5-phosphatase was decreased twofold compared with the wild-type enzyme (FIG. 10A). However, the stability of the protein was not significantly affected (FIGS. 10B & 10C). Taking these data together, OCRL is shown to interact with TRPV4 calcium channel and both proteins localize within the primary cilia.

Example 6

In this Example, the dependence of TRPV4 on OCRL for responding to mechanosensory signals to transport $Ca^{2+}$ was analyzed.

For calcium flow experiments, HTM cells and NHF cells were first incubated in 3% BSA in PBS and stained with Fura2 dye for 1 hour. $Ca^{2+}$ flux was induced by laminar flow gradient (16 μl/s) over the cell surface, which bends cilia, followed by 10 mM KCl. Cells were imaged for calcium during flow. Calcium flux was also measured by F340/380 ratio in HTM cells and NHF cells after treatment with the 0.1 μM TRPV4 agonist GSK1016790A. Results presented represent calcium mobilization in three independent experiments.

Figure 11A:
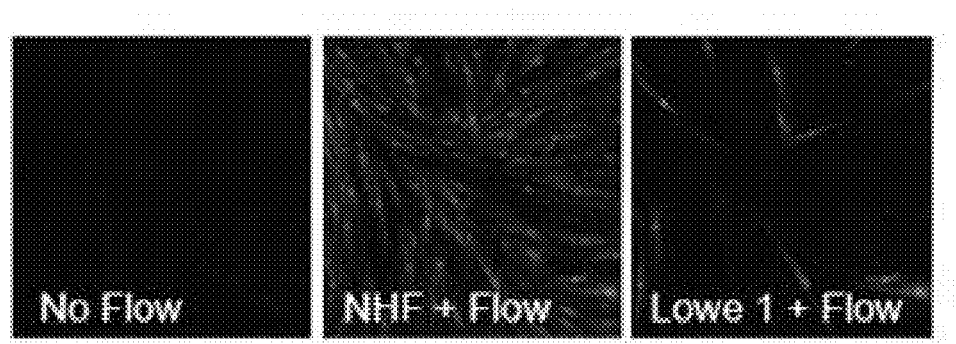
FIG. 11A are micrographs of HTM (Lowe 1) cells and NHF cells stained with Fura2 to visualize calcium flow, as discussed in Example 6. Scale bar=10 μm.
Figure 11B:
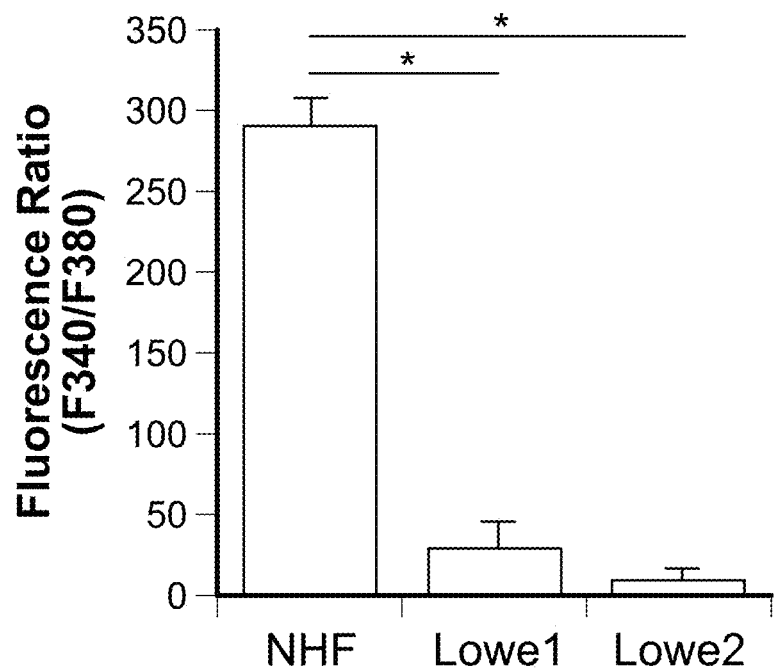
FIG. 11B is a graph illustrating fluorescence ratio of F340/F380 levels as an indication of calcium mobilization in NHF, Lowe 1 and Lowe 2 cells stained with Fura2 followed by treatment with 0.1 μM of the TRPV4 agonist GSK1016790A, as discussed in Example 6. Error bars represent standard deviation.

In Fura2-loaded HTM cells and NHF cells, $Ca^{2+}$ flux was induced by laminar flow gradient (FIG. 11A). Calcium flux as measured by F340/380 ratio in NHF cells was also elicited by treatment with the TRPV4 agonist GSK1016790A (FIG. 11B). However, this TRPV4 agonist failed to elicit calcium mobilization in Lowe patient fibroblasts.

Figure 12A:
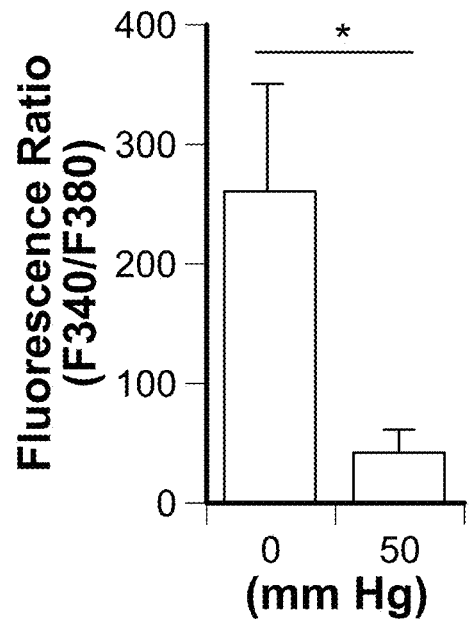
FIG. 12A is a graph illustrating defective TRPV4-mediated calcium signaling in HTM cells under elevated pressure, as discussed in Example 6.

HTM cells treated, with or without pressure, were further evaluated to determine their response to TRPV4 agonist. HTM cells were serum-starved for 48 hours to induce ciliogenesis, followed by treatment with 0 or 50 mmHg for 3 hours. Cells were loaded with Fura-2 AM dye for 1 hour, followed with 0.1 μM TRPV4 agonist GSK1016790A. The ratio of F340/380 (value×1000) that indicates calcium mobilization is shown in FIG. 12A. Particularly, in ciliated HTM cells treated with 50 mmHg hydrostatic pressure, a significant decrease in TRPV4-induced calcium flux was observed.

Figure 12B:
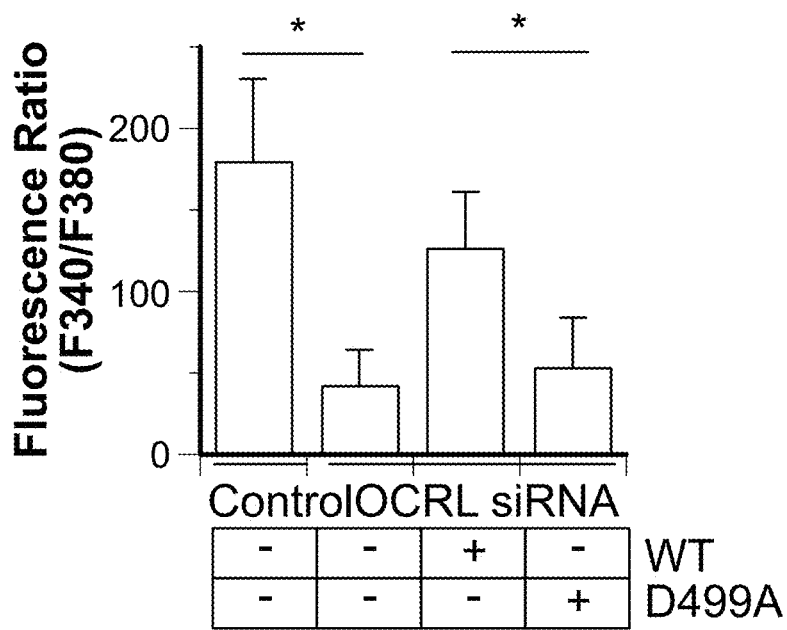
FIG. 12B is a graph illustrating TRPV4-mediated calcium signaling in HTM cells, as discussed in Example 6.

OCRL is required for TRPV4-mediated calcium signaling in HTM cells. HTM cells were additionally treated with OCRL siRNA or scrambled control siRNA, with or without wild-type OCRL or OCRL-D499A rescue. 0.1 μM TRPV4 agonist GSK1016790A treatment was performed and calcium mobilization by F340/380 (value×1000) was measured and shown. As shown in FIG. 12B, a decrease in F340F380 fura-2 signaling was observed using OCRL siRNA or scrambled control siRNA-treated HTM cells in the presence of TRPV4-agonist, which was rescued by wild-type OCRL, but not by the D499A mutant.

Figure 12C:
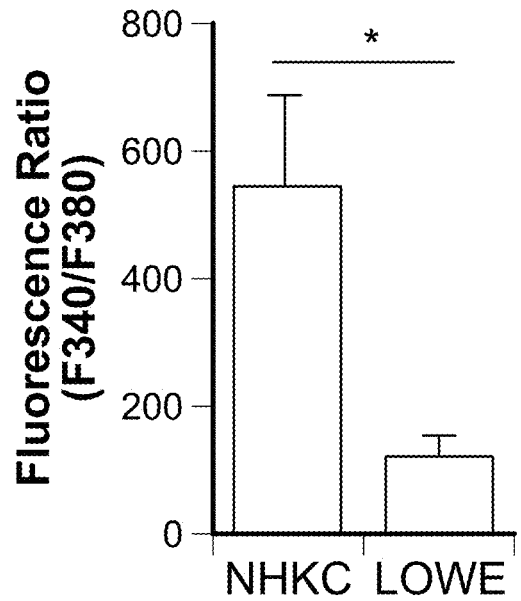
FIG. 12C is a graph illustrating defective TRPV4-mediated calcium flux in Lowe syndrome patient cells, as discussed in Example 6.

Additionally, a Lowe syndrome patient's keratinocytes were isolated and assayed for their response to TRPV4 treatment. NHKC or Lowe keratinocytes were serum-starved, loaded with Fura-2 AM and then treated with 0.1 μM TRPV4 agonist GSK1016790A. F340/380 ratio (value× 1000) was determined. The treatment with TRPV4 agonist failed to elicit calcium mobilization in Lowe patient keratinocytes compared with normal keratinocytes (FIG. 12C).

Based on the results presented above, the functional consequences of activating TRPV4 on eye pressure were therefore assessed in the wpk rat model. The wpk rat is a well-established model for studying ciliopathy, as these animals develop hydrocephalus that responds to cilia-based therapy.

8-day old wpk$^{-/-}$ rats were treated with sham, TRPV4 agonist (50 ng/g, GSK 1016790A), or antagonist (HC 067047) once per day for 8 days. At day 17, intraocular pressure measurements (in mmHg) were performed using a Tonolab tonometer 24 hours after treatment.

Figure 11C:
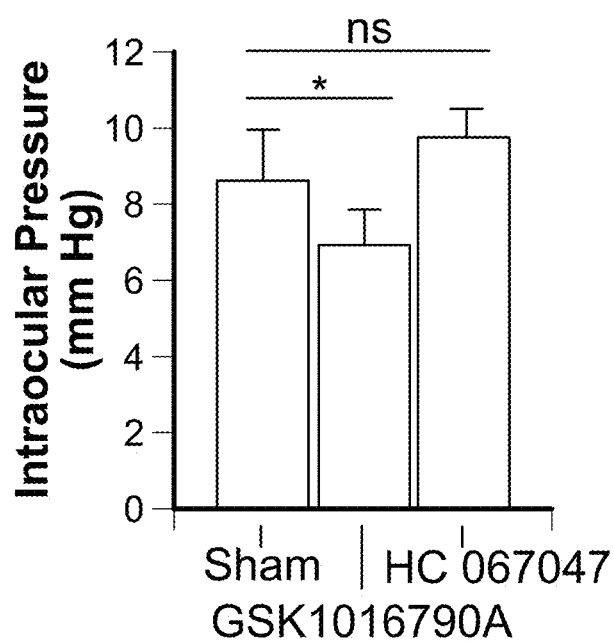
FIG. 11C is a graph illustrating intraocular pressure in wtpk$^{-/-}$ rats that were sham treated, treated with the TRPV4 agonist GGSK 1016790A, and treated with the TRPV4 antagonist HC 067047, as discussed in Example 6. Error bars represent standard deviation, unpaired t-test, *, p<0.001.

In 17-day-old wpk$^{-/-}$ rats, intraocular pressure was significantly reduced with systemic GSK1016790A treatment but not by sham treatment or with a TRPV4 antagonist (HC 067047) (FIG. 11C).

Figure 12D:
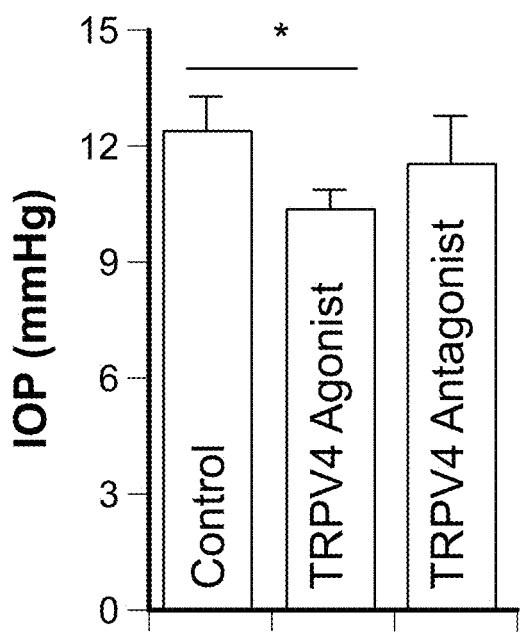
FIG. 12D is a graph illustrating that TRPV4 agonist, but not an antagonist, lowers IOP in mouse, as discussed in Example 6.

This finding was confirmed in wild-type C5BL/6 mice treated with systemic TRPV4 agonist, antagonist, or sham control, daily over 4 days. Nine-week old C57BL/6 WT mice were treated with sham, TRPV/4 agonist GSK 1016790A or antagonist HC 067047 for 4 days. IOP was measured using a Tonolab tonometer 24 hours after treatment. As shown in FIG. 12D article, a decrease in IOP from 12.4 to 10.3 mmHg was seen.

Figure 12E:
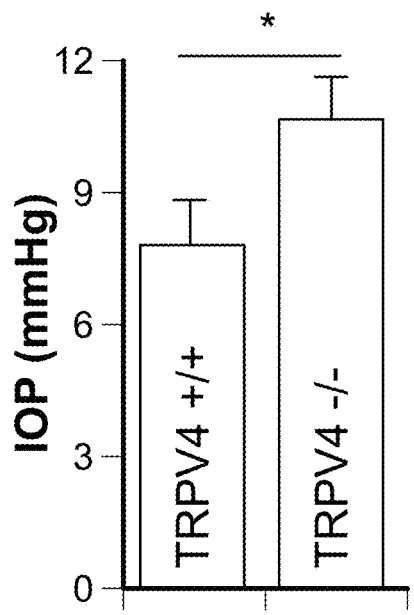
FIG. 12E is a graph illustrating that TRPV4$^{-/-}$ mice exhibited higher IOP than TRPV4+/+ mice, as discussed in Example 6.
Figure 12F:
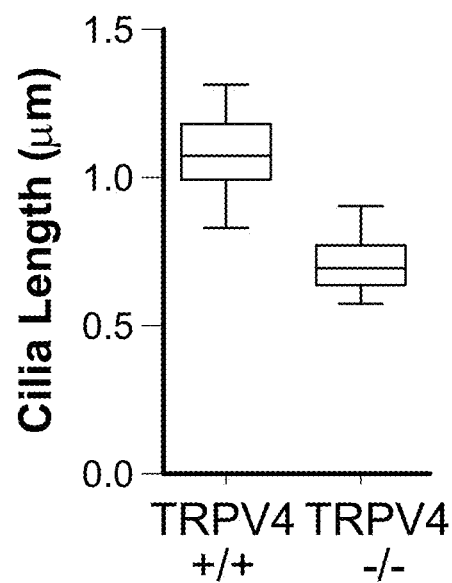
FIG. 12F is a graph illustrating shortened cilia in TM cells of TRPV4$^{-/-}$, as discussed in Example 6.
Figure 12G:
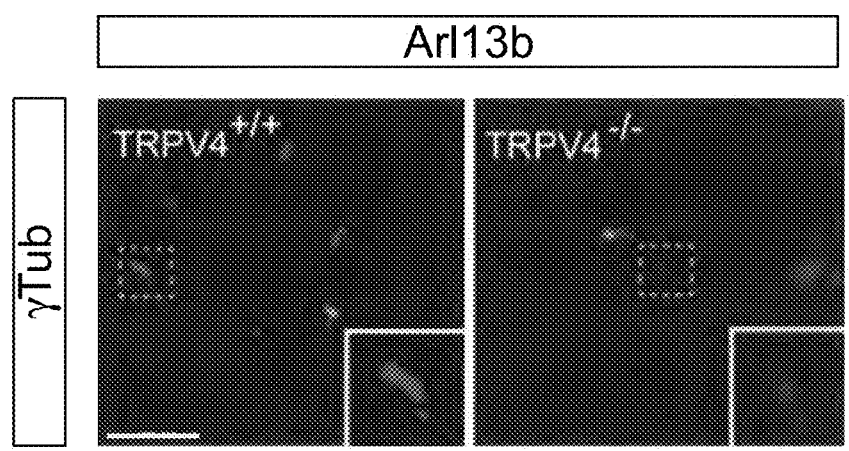
FIG. 12G are fluorescence micrographs of shortened cilia in TM cells of TRPV4$^{-/-}$, as discussed in Example 6.

Finally, IOP was assessed in 7-month old TRPV4$^{+/+}$ versus TRPV4$^{-/-}$ mice. IOP in TRPV4$^{-/-}$ mice was shown to be elevated compared with control TRPV4$^{+/+}$ mice (FIG. 12E). The primary cilia in the TM of these animals were evaluated by immunofluorescence staining for ciliary markers with Arl13b and γ-tubulin; the cilia were found to be indeed shorter in the TRPV4$^{-/-}$ mice (FIGS. 12F & 12G). These results indicated that functional OCRL is necessary for TRPV4 distribution, which in turn is required for calcium signaling and cilia growth in response to mechanical stimuli.

Example 7

In this Example, additional TRPV4 agonists and antagonists were analyzed.

Figure 13A:
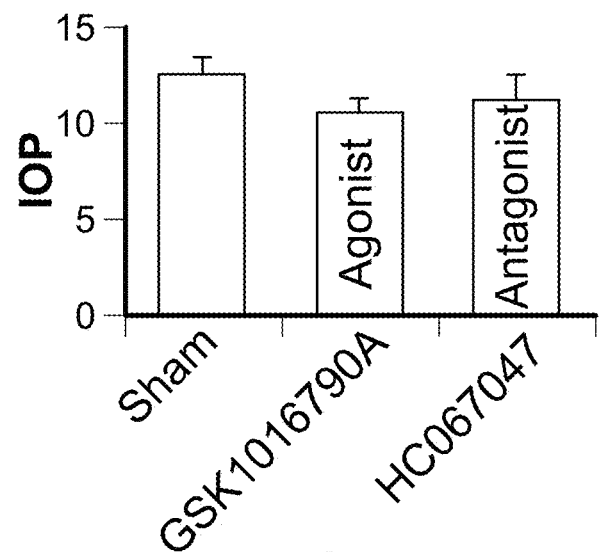
FIGS. 13A & 13B are graphs illustrating the effect of TRPV4 agonists and antagonists on IOP lowering effect in C57Bl/6 mice, as discussed in Example 7.
Figure 13B:
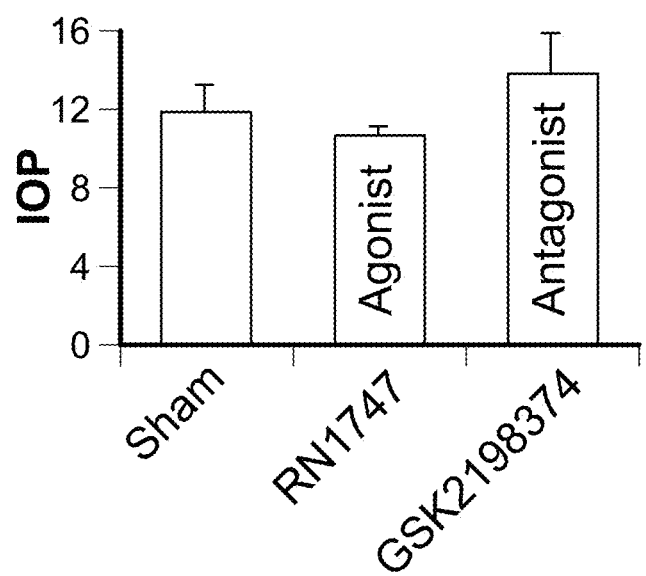

Both agonists and antagonists were diluted in PBS to indicated concentrations and given i.p. to animals as shown in FIGS. 13A & 13B. IOP measurements were performed with TONOLAB®. As shown in FIGS. 13A & 13B, only TRPV4 agonists have an IOP lowering effect.

Example 8

In this Example, a time-dependent analysis using TRPV4 agonists are conducted.

Figure 14A:
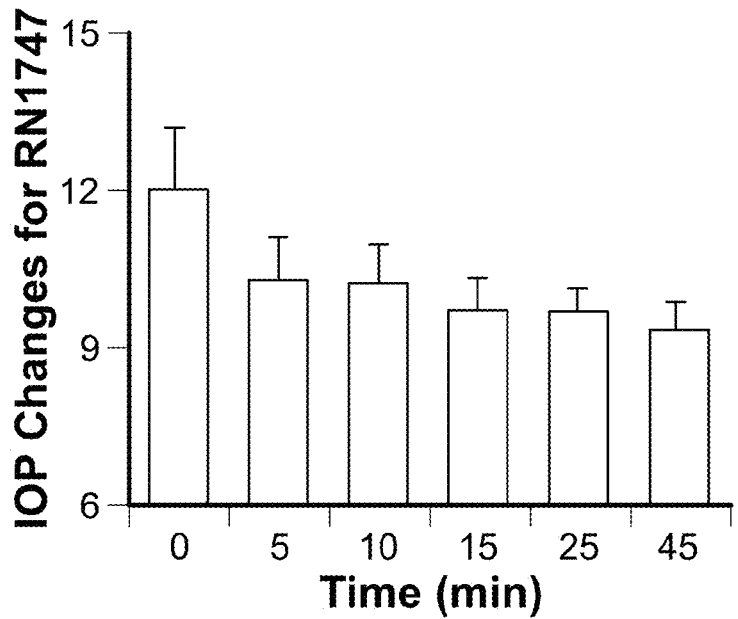
FIGS. 14A & 14B are graphs illustrating the time-dependent lowering effect of TRPV4 agonists, as discussed in Example 8.
Figure 14B:
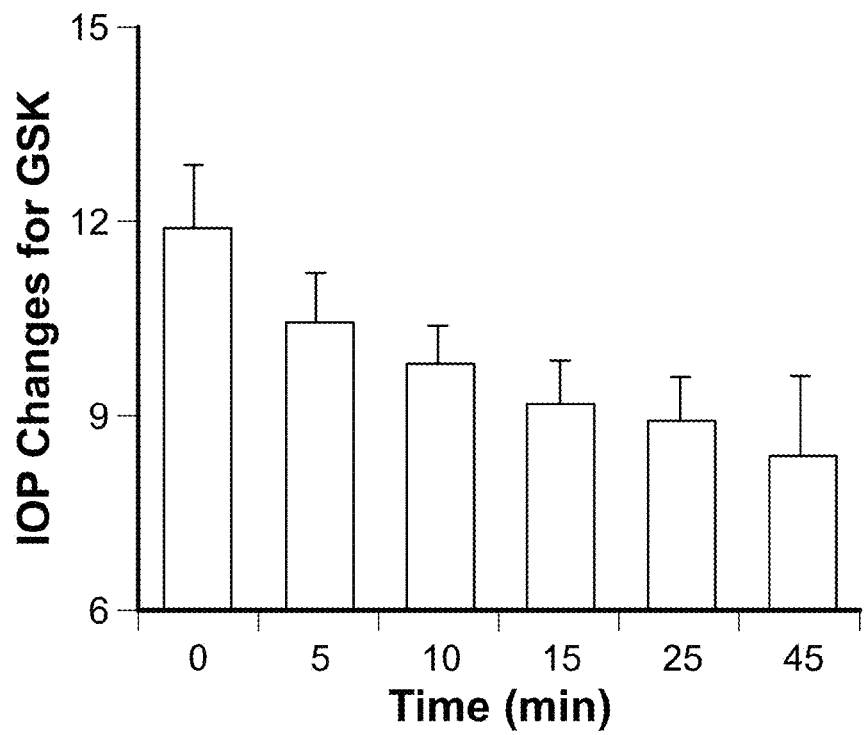

Both agonists and antagonists were diluted in PBS to indicated concentrations and given i.p. to animals as shown in FIGS. 14A & 14B. IOP measurements were performed with TONOLAB®. As shown in FIGS. 14A & 14B, IOP-lowering effect is increased within 45 minutes of administration of the TRPV4 agonists.

Example 9

In this Example, TRPV4 distribution in human trabecular meshwork (TM) cilia is analyzed.

Figure 15:
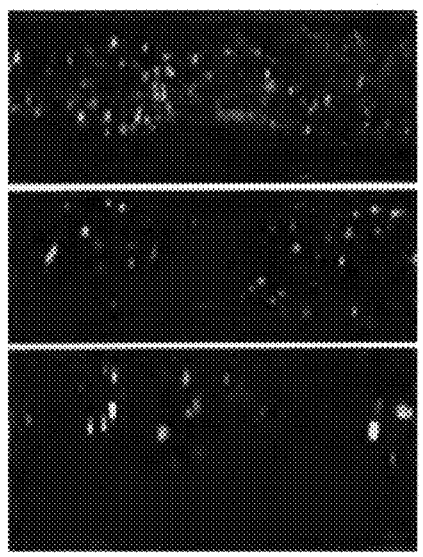
FIG. 15 are fluorescence micrographs illustrating the expression of TRPV4 in human TM cells, as discussed in Example 9.

Cilia counting was performed on the fluorescent images. Student t-test was used to compare the two groups. As shown in FIG. 15, the TRPV4 distribution in human TM cilia support its function as a mechanosensor in the eye. Based on the results, TRPV4 trafficking to the cilia is an essential step for the release of intracellular calcium, which may lead to subsequent enhanced $Ca^{2+}$/calmodulin-dependent protein kinase II activity and up-regulate endothelial nitric oxide synthase. Nitric oxide has been shown as an effector path-way for lowering intraocular pressure. Accordingly, it is believed that the primary cilia within TM cells may serve as an afferent pathway for signal transduction.

Figure 16:
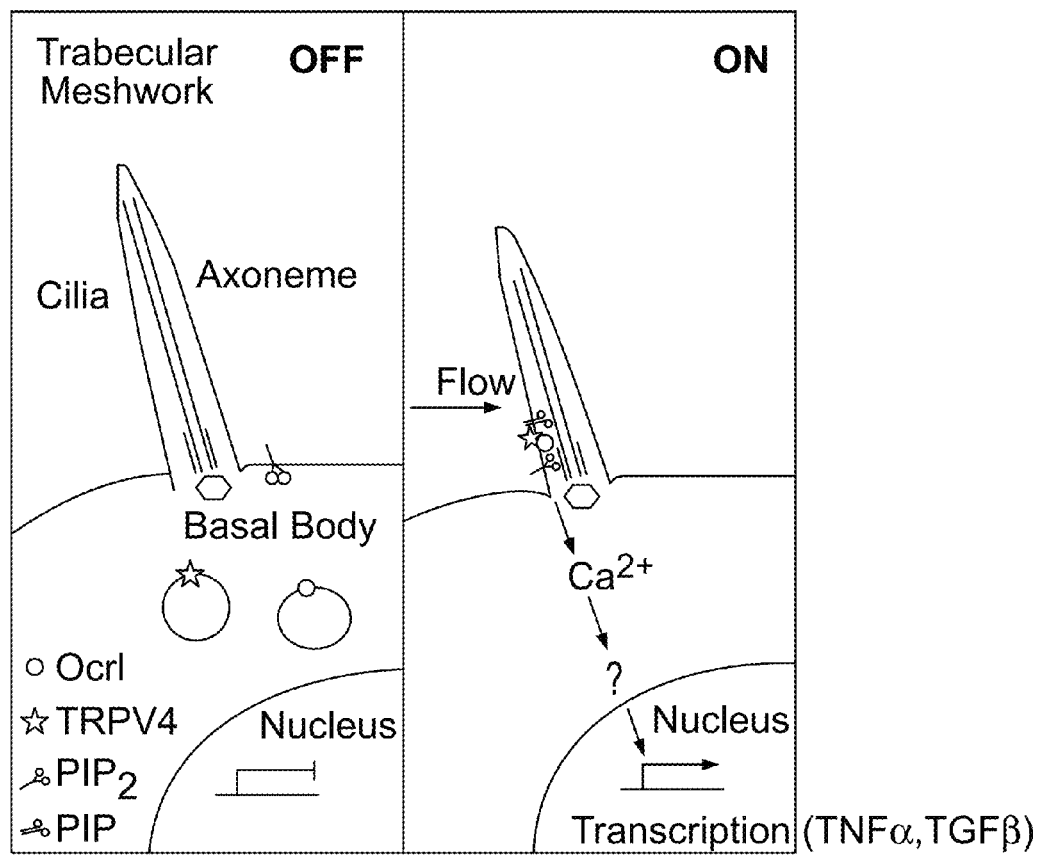
FIG. 16 is an illustration of a model for OCRL and TRPV4 in the cilia of trabecular meshwork cells.

Mechanosensation of pressure underlies a number of important human diseases including the development of hypertension and glaucoma. Defective sensation of pressure may result in imbalance of aqueous humor, resulting in elevated intraocular pressure. Low levels of eye pressure result in structural changes of the retina and poor vision, while elevated eye pressure may damage the optic nerve. As illustrated in the schematic presented in FIG. 16, a role of primary cilia in the sensation of pressure in human TM is presented. The presence of cilia that shortened in response to pressure in TM cells was identified and proper cilia function was determined to be essential for pressure sensation in these cells. These effects were found to require both OCRL and TRPV4 in a manner where OCRL contributed to proper localization and function of TRPV4 in the cilia. This, in turn, is necessary for calcium flux that regulates the transcriptional programs that coordinate cilia function with pressure sensing. As provided herein, cilia in the TM cells regulated pressure of the eye, which, when dysregulated, is strongly implicated in the pathogenesis of glaucoma.

These results surprisingly allow for the treatment of intraocular pressure and, in particular, glaucoma. The present disclosure has a broad and significant impact, as it allows for treating glaucoma and dysregulation of eye pressure that can lead to vision loss and blindness.

What is claimed is:

1. A method for reducing intraocular pressure in an individual in need thereof, the method comprising: administering a composition comprising a transient receptor potential cation channel subfamily V member 4 (TRPV4) agonist to the individual, wherein the TRPV4 agonist is (N-((1S)-1-{[4-((2S)-2-{[(2,4-dichlorophenyl)sulfonyl]amino}-3-hydroxypropanoyl)-1-piperazinyl]carbonyl}-3-methylbutyl)-1-benzothiophene-2-carboxamide).

2. The method of claim 1, wherein the individual is administered from about 50 ng/g body weight to about 500 ng/g body weight of the TRPV4 agonist.

3. The method of claim 1, wherein the individual is administered the TRPV4 agonist using a method selected from the group consisting of topically, periocularly, intraocularly, and combinations thereof.

4. The method of claim 3, wherein the individual is administered the TRPV4 agonist using intraocular injection.

5. A method for treating glaucoma in an individual in need thereof, the method comprising: administering a composition comprising a transient receptor potential cation channel subfamily V member 4 (TRPV4) agonist to the individual, wherein the TRPV4 agonist is (N-((1S)-1-{[4-((2S)-2-{[(2,4-dichlorophenyl)sulfonyl]amino}-3-hydroxypropanoyl)-1-piperazinyl]carbonyl}-3-methylbutyl)-1-benzothiophene-2-carboxamide).

6. The method of claim 5, wherein the individual is administered from about 50 ng/g body weight to about 500 ng/g body weight of the TRPV4 agonist.

7. The method of claim 5, wherein the individual is administered the TRPV4 agonist using a method selected from the group consisting of topically, periocularly, intraocularly, and combinations thereof.

8. The method of claim 7, wherein the individual is administered the TRPV4 agonist using intraocular injection.

9. A method for treating a ciliopathy in an individual in need thereof, the method comprising: administering a composition comprising a TRPV4 agonist to the Individual, wherein the TRPV4 agonist is (N-((1S)-1-{[4-((2S)-2-{[(2,4-dichlorophenyl)sulfonyl]amino}-3-hydroxypropanoyl)-1-piperazinyl]carbonyl}-3-methylbutyl)-1-benzothiophene-2-carboxamide).

10. The method of claim 9, wherein the individual is administered from about 50 ng/g body weight to about 500 ng/g body weight of the TRPV4 agonist.

11. The method of claim 9, wherein the individual is administered the TRPV4 agonist using a method selected from the group consisting of topically, periocularly, intraocularly, and combinations thereof.

12. The method of claim 11, wherein the individual is administered the TRPV4 agonist using intraocular injection.

13. The method of claim 9, wherein the ciliopathy is selected from the group consisting of retinitis pigmentosa, renal cysts, polydactyly, and developmental delays.

* * * * *

SEQUENCE LISTING

```
<160> NUMBER OF SEQ ID NOS: 3

<210> SEQ ID NO 1
<211> LENGTH: 8
<212> TYPE: PRT
<213> ORGANISM: Homo sapiens

<400> SEQUENCE: 1

Pro Ala Trp Cys Ala Arg Ile Leu
1               5

<210> SEQ ID NO 2
<211> LENGTH: 25
<212> TYPE: DNA
<213> ORGANISM: Homo sapiens

<400> SEQUENCE: 2
aggtcggacc acacgggctt aagaa                                          25
```

```
<210> SEQ ID NO 3
<211> LENGTH: 25
<212> TYPE: DNA
<213> ORGANISM: Homo sapiens

<400> SEQUENCE: 3
tccagcctgg tgtgcccgaa ttctt                                          25
```